(12) United States Patent
Maani et al.

(10) Patent No.: US 11,986,322 B2
(45) Date of Patent: *May 21, 2024

(54) HEART RATE PATH OPTIMIZER

(71) Applicant: Apple Inc., Cupertino, CA (US)

(72) Inventors: Ehsan Maani, San Jose, CA (US); Daniel J. Culbert, Los Gatos, CA (US); Ian R. Shapiro, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 640 days.

This patent is subject to a terminal disclaimer.

(21) Appl. No.: 15/848,602

(22) Filed: Dec. 20, 2017

(65) Prior Publication Data

US 2018/0110469 A1 Apr. 26, 2018

Related U.S. Application Data

(63) Continuation of application No. 14/466,890, filed on Aug. 22, 2014, now Pat. No. 9,867,575.

(51) Int. Cl.
*A61B 5/00* (2006.01)
*A61B 5/0205* (2006.01)
*A61B 5/024* (2006.01)
*A61B 5/11* (2006.01)

(52) U.S. Cl.
CPC ............ *A61B 5/721* (2013.01); *A61B 5/0205* (2013.01); *A61B 5/024* (2013.01); *A61B 5/11* (2013.01); *A61B 5/725* (2013.01); *A61B 5/7257* (2013.01); *A61B 5/7278* (2013.01); *A61B 5/02416* (2013.01); *A61B 2560/0493* (2013.01); *A61B 2562/0219* (2013.01)

(58) Field of Classification Search
CPC ....... A61B 5/72; A61B 5/7221; A61B 5/7232; A61B 5/7253–5/726; A61B 5/7246
USPC .......................................................... 702/19
See application file for complete search history.

(56) References Cited

U.S. PATENT DOCUMENTS

| | | | |
|---|---|---|---|
| 5,483,261 A | 1/1996 | Yasutake | |
| 5,488,204 A | 1/1996 | Mead et al. | |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,663,607 B2 | 2/2010 | Hotelling et al. | |
| 8,479,122 B2 | 7/2013 | Hotelling et al. | |
| 2005/0049470 A1 | 3/2005 | Terry | |
| 2006/0197753 A1 | 9/2006 | Hotelling | |
| 2012/0190948 A1 | 7/2012 | Vetter et al. | |
| 2012/0302900 A1 | 11/2012 | Yin et al. | |
| 2014/0213863 A1 | 7/2014 | Loseu et al. | |
| 2016/0051201 A1 | 2/2016 | Maani et al. | |

FOREIGN PATENT DOCUMENTS

| | | |
|---|---|---|
| CN | 201664305 | 12/2010 |
| CN | 104739422 | 7/2015 |
| JP | 2000-163031 A | 6/2000 |
| JP | 2002-342033 A | 11/2002 |
| WO | WO 05/020798 | 3/2005 |

OTHER PUBLICATIONS

Periyasamy, V., Pramanik, M. & Ghosh, P.K. "Review on Heart-Rate Estimation from Photoplethysmography and Accelerometer Signals During Physical Exercise." J Indian Inst Sci 97, 313-324 (2017) (Year: 2017).*
Tamura, Toshiyo, et al. "Wearable photoplethysmographic sensors—past and present." Electronics 3.2 (2014): 282-302 (Year: 2014).*
Mukhopadhyay, Subhas Chandra. "Wearable sensors for human activity monitoring: A review." IEEE sensors journal 15.3 (2014): 1321-1330 (Year: 2014).*
Hongwei, H., "Design and Analysis of Algorithms," Dynamic Programming, Xidian University, CLRS Chapter 15, 24 pages, publicly available prior to Aug. 22, 2014.
Barto, A. G. et al. (May 1, 1985). "Pattern-Recognizing Stochastic Learning Automata," IEEE Transactions on Systems, Man and Cybernetics, IEEE Inc. New York, US, vol. SMC-15, No. 3, pp. 360-375, the whole document.
DeBoer, R. et al. (Apr. 1984). "Comparing Spectra of a Series of Point Events Particularly for Heart Rate Variability Data," IEEE Transactions on Biomedical Engineering, vol. BME-31, No. 4, four pages.
European Search Report dated Jan. 20, 2016, for EP Patent Application No. 15179619.0, twelve pages.
Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
Lopèz-Silva, S. M. et al. (2012). "Heuristic Algorithm for Photoplethysmographic Heart Rate Tracking During Maximal Exercise Test," *Journal of Medical and Biological Engineering* vol. 32:3, pp. 181-188.

(Continued)

*Primary Examiner* — G. Steven Vanni
(74) *Attorney, Agent, or Firm* — Brownstein Hyatt Farber Schreck, LLP

(57) ABSTRACT

A device for determining a heart rate of a user has a PPG sensor and an accelerometer to compensate for acceleration artifacts within the PPG signal. The device transforms time domain PPG and accelerometer signals into the frequency domain using a Fourier transformation and utilizes the Fourier coefficient magnitudes as indicative of the probability of candidate heart rate values. Candidate heart rate values are determined at sampling times over a time interval and a most probable heart rate path during the time interval is determined using a reward/penalty algorithm.

20 Claims, 16 Drawing Sheets

(56) References Cited

OTHER PUBLICATIONS

Non-Final Office Action dated Feb. 21, 2017, for U.S. Appl. No. 14/466,890, filed Aug. 22, 2014, eleven pages.
Notice of Allowance dated Sep. 11, 2017, for U.S. Appl. No. 14/466,890, filed Aug. 22, 2014, five pages.
Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.
Rubine, D.H. (May 1992). "Combining Gestures and Direct Manipulation," CHI '92, pp. 659-660.
Thakare, R. D., et al. (Apr. 2014). "DSP Based ECG Abnormality Classification using Artificial Neural Network," International Journal of Advanced Research in Computer Science and Software Engineering, Research Paper, vol. 4, Issue 4, located at: www.ijarcsse.com, pp. 582-586.
Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

HEART RATE PATH OPTIMIZER

CROSS REFERENCES TO RELATED APPLICATIONS

This application is a continuation of U.S. patent application Ser. No. 14/466,890, filed Aug. 22, 2014 and published on Feb. 25, 2016 as U.S. Patent Publication No. 2016-0051201, the contents of which are incorporated herein by reference in its entirety for all purposes.

FIELD OF THE DISCLOSURE

This relates generally to processing of a photoplethysmogram (PPG) signal and for determining the most probable heart rate at various times within a sampling time interval.

BACKGROUND OF THE DISCLOSURE

A photoplethysmogram (PPG) signal may be obtained from a pulse oximeter, which employs a light emitter and a light sensor to measure the perfusion of blood to the skin of a user. The PPG signal may be compromised by noise due to motion (e.g., acceleration) artifacts. That is, movement of the body of a user may cause the skin and vasculature to expand and contract, introducing acceleration artifacts into the PPG signal. While such acceleration artifacts may be at least partially compensated for, there remains a problem of determining accurate heart rate measurements even after such partial compensation. When presented with various heart rate values over sampling times within a time interval, it is often difficult to determine the most probable heart rate for each sampling time and consequently the most probable heart rate path considering the multiple possible candidate paths from one sampling time to the next over the overall time interval.

SUMMARY OF THE DISCLOSURE

A photoplethysmogram (PPG) signal may be obtained from a pulse oximeter, which employs a light emitter and a light sensor to measure the perfusion of blood to the skin of a user. However, the signal may be compromised by noise due to motion artifacts especially artifacts caused by acceleration. That is, movement of the body of a user may cause the skin and vasculature to expand and contract, introducing noise to the signal. To address the presence of motion artifacts, examples of the present disclosure can utilize an accelerometer to measure movements of the user and signal processing of the PPG signal in combination with the accelerometer signal to at least partially compensate for unwanted artifacts.

While most acceleration artifacts may be taken into account and compensated for, they are sometimes difficult to eliminate completely. Thus, there remains a problem in that it can be difficult to determine accurate heart rate values over plural sampling times during a time interval, as for example an exercise time interval.

In accordance with some examples of the disclosure, time domain PPG and acceleration signals can be digitized and transformed into the frequency domain by utilization of a Fourier transform such as the Fast Fourier Transform to provide spectrograms. The magnitude (absolute value) of a given Fourier coefficient of frequency f represents the probability of occurrence of that frequency f in the time domain signal. Thus, the identification of the highest Fourier coefficient magnitude corresponds to the peak in the spectrogram of frequency f and corresponds to the most probable heart rate having this frequency f.

Accurate identification of the heart rate at each sampling time period is often improved by examining subsequent data and reevaluating the earlier determined heart rate in view of this subsequent data. Thus, the earlier data may be viewed as candidate heart rates which are provisionally determined for later confirmation or selection of the more correct heart rate. The series of candidate heart rates over a given time period presents candidate heart rate paths. In accordance with examples disclosed herein, the heart rate paths may be evaluated under certain rules to determine the most probable heart rate path, and thus by back-tracking, make a most probable selection of the heart rate among the provisionally determined candidate heart rates. The rules used to evaluate the candidate heart rate paths involve a reward of paths proportional to the sum of Fourier coefficient magnitudes taken by the path (such that the most probable frequencies, i.e., heart rates) are chosen, and a penalty for the paths proportional to changes in the heart rate between consecutive sampling times (such that large jumps in heart rate between consecutive sampling times are less likely).

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

A photoplethysmogram (PPG) signal may be obtained from a pulse oximeter, which employs a light emitter and a light sensor to measure the perfusion of blood to the skin of a user. However, the signal may be compromised by noise due to motion artifacts especially artifacts caused by acceleration. That is, movement of the body of a user may cause the skin and vasculature to expand and contract, introducing noise to the signal. To address the presence of motion artifacts, examples of the present disclosure utilize an accelerometer to measure movements of the user and signal processing of the PPG signal in combination with the accelerometer signal to compensate for unwanted artifacts.

Figure 1:
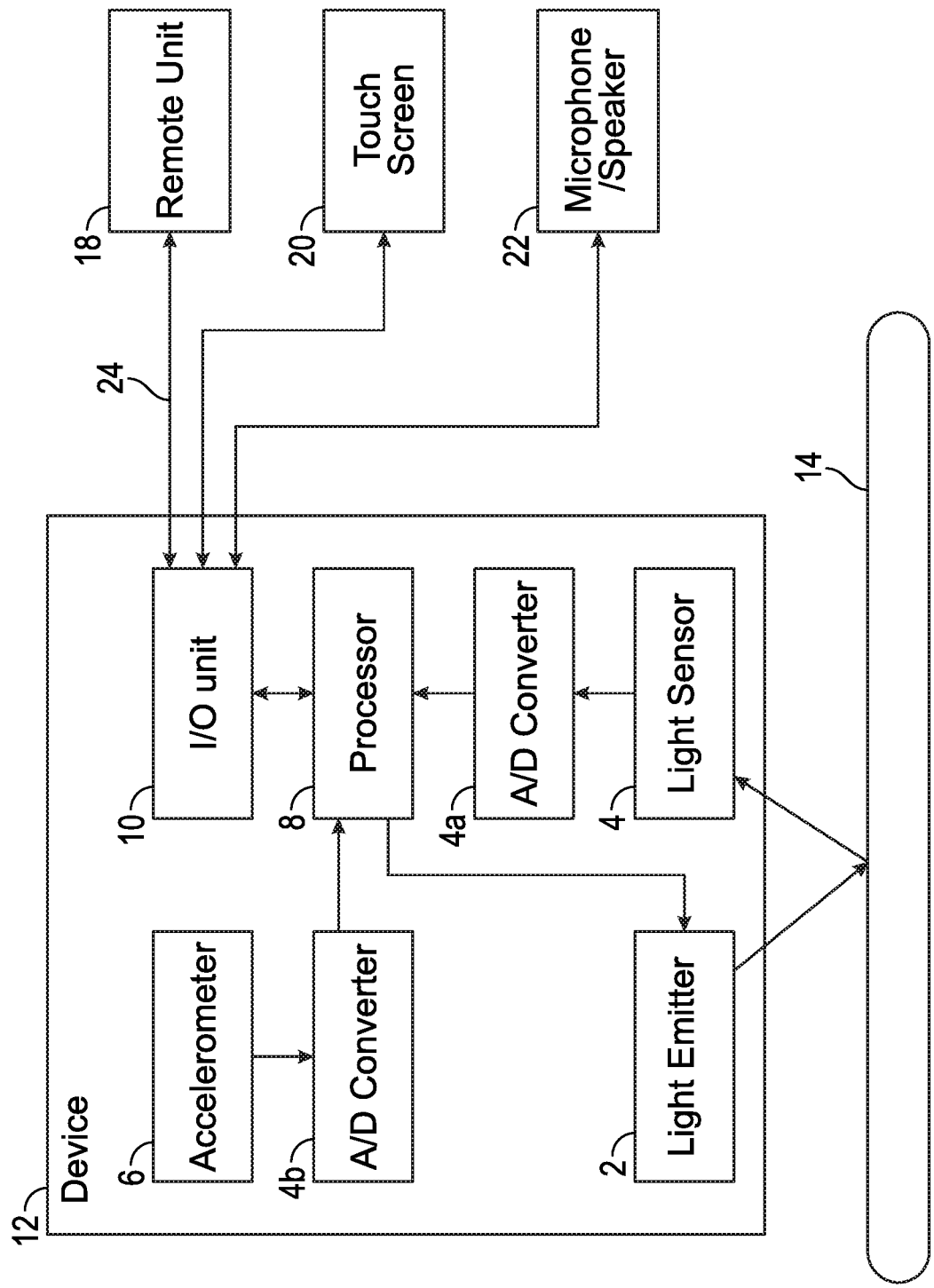
FIG. 1 shows an overall block diagram of the heart rate measuring and path optimization device used in various examples of the disclosure.

FIG. 1 is an overall block diagram of some examples of the disclosure and is seen to illustrate a light emitter 2, light sensor 4, A/D converter 4a, accelerometer 6, processor 8 and I/O unit 10. These devices may be incorporated within a physical device 12 that is worn or held by a user such as being secured to a user's skin (a limb for example) or otherwise attached to an article of clothing worn by the user, with the light emitter 2 and light sensor 4 being positioned proximate a user's skin. Alternately, the device 12 may be entirely or partially incorporated within a smartphone such that a user can hold the smartphone in a manner to cause the below described light beam to be reflected from the user's skin back into a light sensor positioned within the smartphone itself. A portion of the light from a light emitter 2 may be absorbed by the skin, vasculature, and/or blood, among other possibilities, and a portion may be reflected back to a light sensor 4 co-located with the light emitter. The light sensor 4 can be situated in a line parallel to a blood pulse wave, and the signals from the sensor 4 can include heart rate (HR) signals due to the pulse wave.

The accelerometer 6 can provide time domain acceleration output signals indicative of acceleration movements of the user. For example, the device 12 may be worn on a user's wrist, and the accelerometer output signals can be indicative of the arm movements (i.e., arm swings) made by the user.

In operation, the light emitter 2 can transmit a light beam to the user's skin 14, and the light beam can be reflected by the user's skin 14 and received by the light sensor 4. The light sensor 4 can convert this light into an electrical signal indicative of the intensity thereof. This electrical signal can be in analog form and can be converted into digital form by A/D converter 4a. The digital signal from the A/D converter 4a can be a time domain PPG heart rate (HR) signal which is fed to the processor 8. The outputs of the accelerometer 6 can also be converted to digital form using A/D converter 4b. The processor 8 can receive the digitized HR signal from the light sensor 4 and the digitize accelerometer output signals from the accelerometer 6, and can process these signals to provide a HR output signal to the I/O unit 10. The I/O unit 10 may take the form of one or more of a storage device, a visual display, an audible annunciator, a touch screen integral with device 12, or other output indicator. The I/O unit 10 may, under program control from the processor 8, provide historical information in visual (numeric, tabular, graphic) or audible (synthesized voice or tone) form of the detected heart rate over a period of time. As one non-limiting example, a visual graph may be displayed showing the HR calculated for each 5 minutes during a prior fixed time interval (e.g., 1 hr.) or after an exercise period has been completed as determined by an indication thereof from the user. The I/O unit 10, may also provide, under control of the processor 8 average heart rate information or statistical information of the heat rate over a prior time period or periods. As a further example, the I/O unit 10 may provide current heart rate values as "real time" heart rate values displayed to the user periodically (e.g., every second) during the course of an ongoing exercise program.

The I/O unit 10 may be coupled to one or more of remote unit 18, touch screen 20 and microphone/speaker 22 via a wired or wireless communication links 24. The remote unit 18 may be a user smart phone or other I/O device conveniently carried or worn by the user, or may be a distant computer or data server such as the user's home computer or the user's cloud storage service. The I/O unit 10 may receive input from the remote unit 18 or may receive input from the user by means of the touch screen 20 and/or the microphone/speaker 22.

Figure 2:
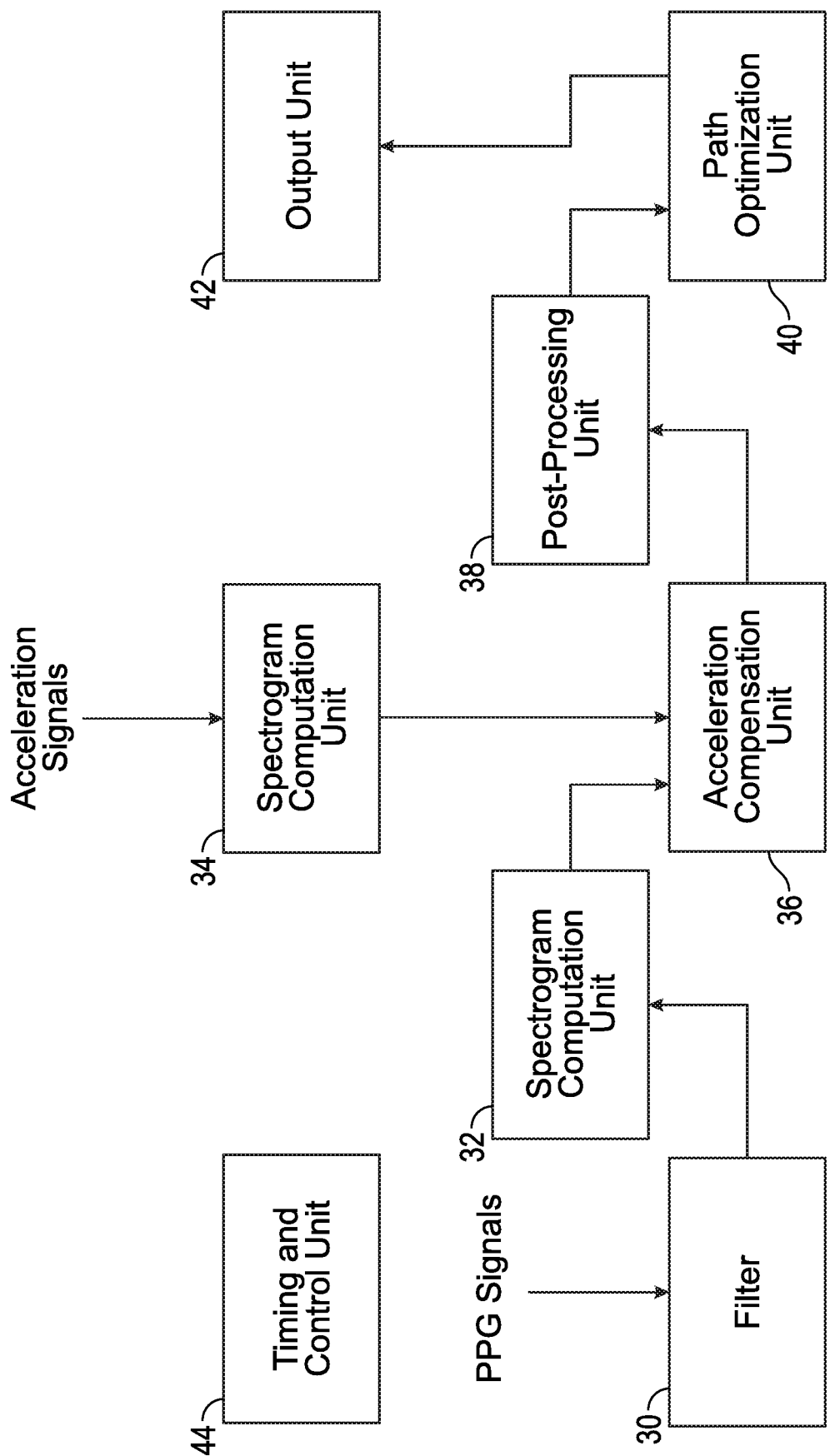
FIG. 2 is an overall flow diagram showing the data flow and computation steps used in determining the heart rate and path optimization in accordance with various disclosed examples.

FIG. 2 is a block diagram of example functional units that can be contained within or controlled by the processor 8 of FIG. 1. These functional units can be implemented as discrete hardware units such as, for example, digital signal processors (DSP), application specific integrated circuits (AISC), field programmable logic arrays (FPGA) or dedicated fast Fourier transform (FFT) integrated circuits. The functional units can be combined into one or more interconnected devices. Alternatively, these functional units can be implemented in the form of software or firmware configured to operate a programmable processor. Further, the functional units can be a combination of discrete hardware, software and firmware.

FIG. 2 is seen to comprise a filter 30, spectrogram computation units 32 and 34, acceleration compensation unit 36, post-processing unit 38, path optimization unit 40, output unit 42 and timing and control unit 44.

The filter 30 can receive the (raw) PPG signals from the light sensor 4 of FIG. 1, which can operate as a PPG sensor of the wearable device 12. These PPG signals can be time domain heart rate (HR) signals having time domain HR components indicative of a user's HR and time domain artifact components. The filter 30 can, for example, be a third order band pass filter having a bandpass of 0.5-8 Hz corresponding to 30-480 bpm (beats per minute). One purpose of the filter 30 can be to remove signals that do not have frequency components that fall within or near the range expected for heart rate monitoring under various expected user conditions or activity levels. The output of the filter 30 can be a filtered PPG signal which can be fed to the spectrogram computational unit 32.

The spectrogram computation unit 32 can convert the filtered PPG signal output from the filter 30 into the frequency, and this conversion can be performed using a fast Fourier transform (FFT). The spectrogram computation unit 32 can take the absolute value of the FFT frequency coefficients by complex conjugation to provide real valued outputs indicative of the magnitudes of the frequency coefficients at each sampling time. Thus, the outputs of the spectrogram computation unit 32 can be frequency domain HR (FDHR) signal magnitudes. The sampling time can be for example, each second.

In a similar fashion, the spectrogram computation unit 34 can convert accelerometer signals (x,y,z) from the accelerometer 6 of FIG. 1 into the frequency domain using a fast Fourier transform (FFT) and can take the absolute value thereof to provide real valued coefficient magnitudes. Thus, outputs of the spectrogram computation unit 34 can be frequency domain accelerometer (FDA) signals magnitudes. The FFT for both the spectrogram computation units 32 and 34 can, for example, be carried out by the same hardware, firmware and/or software and can be computed in parallel or can be time multiplexed to receive the time domain HR signals (PPG signals) and the time domain accelerometer output signals.

The spectrogram computation units 32 and 34 can convert digitized time domain PPG signals into the frequency domain. The time domain signals from the PPG sensor can be sampled periodically by the A/D converters 4a, 4b such as, for example, at a sampling frequency of 128 Hz. A sampling (sliding) window can be established to assemble a fixed number of samples and in some examples, an 8 second window collects a first set of data points, namely 128× 8=1024 sampling points to feed the initial FFT operations by the spectrogram computation units 32, 34. In this way the FFT can be performed with eight seconds worth of data. As new data samples (128 samples at time t=9 seconds) are taken, the first seconds worth of data (128 samples) can be discarded (hence the sliding window) and another FFT can be taken for the second set of 1028 data points. The process can repeat such that each FFT can be taken with respect to a sliding window of 1028 time domain data points. As used hereinbelow a "data sample" generally refers to the output of spectrogram units 32, 34 or 36 (1024 data points) as opposed to the output of the A/D converters. That is, the data samples that are relevant (as used in subsequent FIGS. 3-11) are those in the frequency domain, and these samples, are generated, for example, every second. The data sample is variously termed a spectrogram sample, time sample or simply sample.

The accelerometer compensation unit 36 can receive both the FDHR signal magnitudes from the spectrogram computation unit 32 and the FDA signal magnitudes from the spectrogram computation unit 34, and can compensate the FDHR signal magnitudes based on the FDA signal magnitudes to provide compensated FDHR component magnitudes. In essence, the accelerometer compensation unit 36 acts to compensate the FDHR signal magnitudes in view of the acceleration induced artifacts that can be present in the FDHR signal magnitudes. Such compensation tends to reduce or eliminate the effects of the acceleration induced artifacts, and the details of such compensation are set forth below. The compensated FDHR component magnitudes can be fed to post processing unit 38. The post processing unit 38 can perform one or more of several functions such as harmonic boost, and peak boost to be explained hereinafter. The post processing unit 38 can feed its output as a processed HR signal magnitudes (or alternately termed processed PPG signal magnitudes) to the path optimization unit 40. The path optimizer unit 40 can select the most probable heart rate from the processed HR signal magnitudes and can provide its output to an output unit 42. The output unit 42 can comprise a memory or buffer and an associated I/O device to provide an output suitable for the I/O unit 10 of FIG. 1. The timing and control unit 44 provides various timing and control signals to the other components of FIG. 2 as needed.

In certain examples, FIG. 2 can be implemented as a software program and the various blocks illustrated therein may be understood as steps in a flowchart showing the overall program flow in accordance with the description herein.

Figure 3:
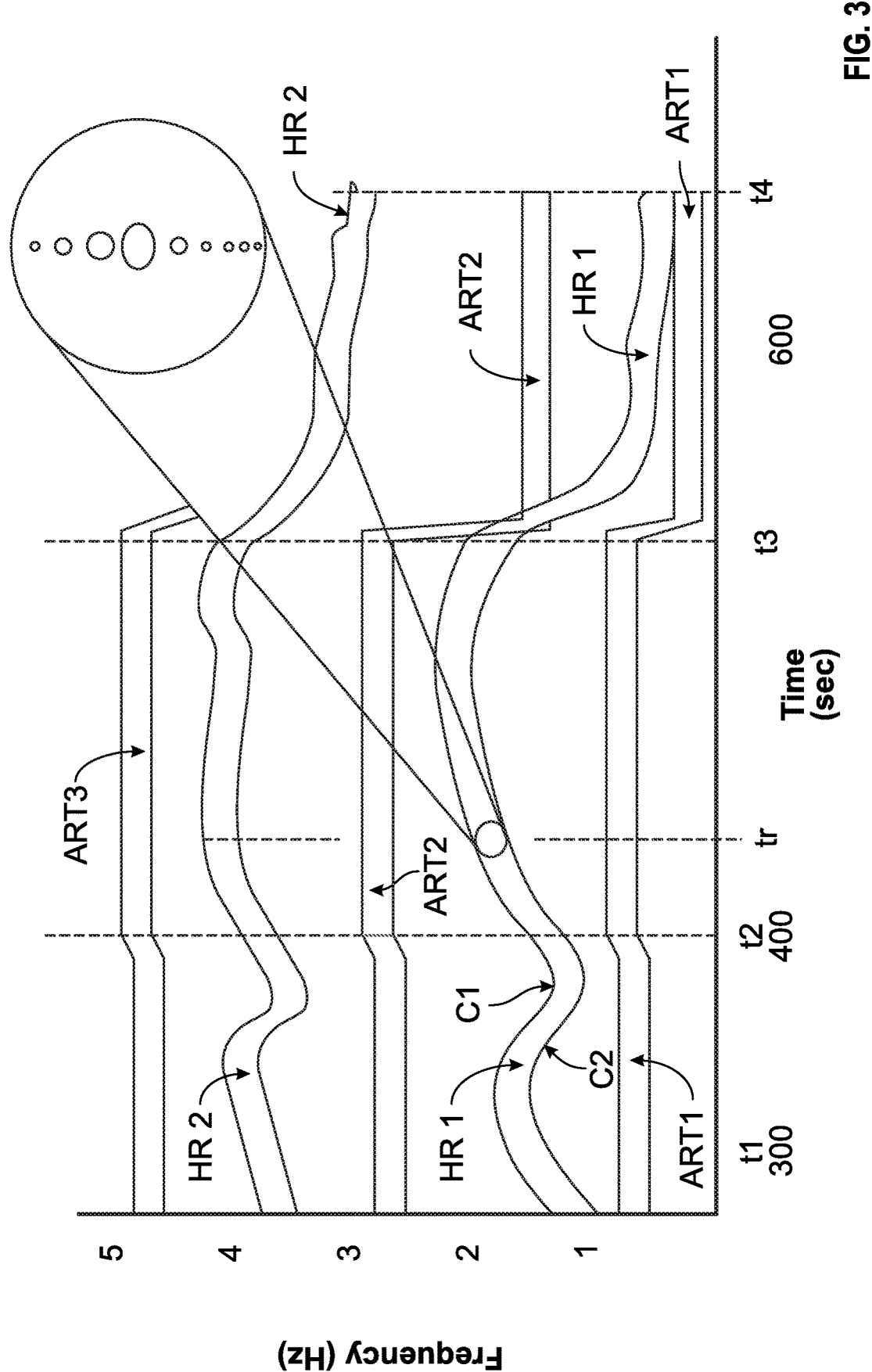
FIG. 3 is a three dimensional illustration of a heart rate spectrogram in accordance with certain examples.

FIG. 3 shows a plot of an exampler FDHR signal magnitudes from spectrogram computation unit 32. FIG. 3 is a three dimensional (3-D) illustration with the x,y coordinates being time (in seconds) and frequency (in Hz) respectively and the third dimension represented by the size of the point (see blowup portion of FIG. 3) corresponding the magnitude (absolute value) of the Fourier coefficient at each x,y point. It may be seen that the plot of the FDHR signal magnitudes from the spectrogram computation unit 32 includes two component magnitudes: (1) frequency domain heart rate (FDHR) component magnitudes represented by regions HR1, HR2 and (2) frequency domain artifact (FDART) component magnitudes represented by regions ART1, ART2, ART3. The HR1 region represents the fundamental frequencies and the HR2 region is the weaker first harmonic. These HR regions represent the true heart rate signal which is desired to be measured. Generally, there will be higher order harmonics (such as second and third order harmonics) as well, but for ease of illustration, and in most practical applications as well, the fundamental and first harmonic are all that need be considered since these higher order harmonics contribute less and less energy to the fundamental. The ART1, ART2, ART3 regions result from acceleration induced artifacts inherent in the PPG sensor signals when the device 12 is worn by a user performing some sort of exercise or motion. These acceleration induced artifacts can be periodic or non-periodic. A periodic acceleration induced artifact may, for example, be produced by the periodic swinging of the users arm if the device 12 is affixed to the user's wrist. A non-periodic accelerations artifact can be produced when a user makes a hand waving motion or gesture. Non-periodic accelerations will generally not have clearly defined harmonic structures. Artifact compensation may be applied to both periodic and non-periodic acceleration in accordance with examples described herein. In FIG. 3 the regions ART1, ART2, ART3 can correspond to a periodic acceleration influence, and as such, the frequency corresponding to these regions is substantially flat corresponding, for example, to a fixed frequency arm motion of the user during relevant time intervals. Each of the HR and ART regions can be represented by an upper and lower curve or envelope. For HR1, the upper and lower curves are identified by C1 and C2 respectively and similar curves (not labeled) bound each of the HR and ART region.

As used herein the word "magnitudes" used in reference to Fourier coefficient is the absolute value of the Fourier coefficient. For example, in the terms FDHR signal magnitudes, FDA signal magnitudes, FDHR component magnitudes FDART component magnitudes, and Fourier coefficients magnitudes the word "magnitude' is meant to correspond to the absolute value of the Fourier coefficients as calculated, for example, by the complex conjugate of the Fourier coefficient so that these magnitudes are real numbers, typically represented by floating point values.

The time axis of FIG. 3 illustrates an example of a first time interval between time t1 and t2 corresponding to the user jogging; an example second time interval between time t2 and t3, corresponding to the user running; and an example third time interval between time t3 and t4 corresponding to the user walking. It may be seen that the frequencies of the Fourier coefficients on the y axis relate to the heart rate by simply multiplying the y axis frequencies by 60 to convert the frequency to beats per minute.

The blowup portion of FIG. 3 shows, in simplified form, the magnitude of the Fourier coefficients of the spectrogram at a representative time tr within region HR1. It may be seen that the larger magnitude coefficients (represented by the larger circles) occur near the center of the upper and lower curves C1, C2 forming the envelope of the region HR1. While the blowup showing the relative magnitude or value of the Fourier coefficients is shown only for region HR1 at representative time tr, it is understood that the spectrogram has coefficient magnitudes (values) all along the representative time tr, that is, not only within region HR1, but also within regions HR2, ART1, ART2, ART3 and even outside of these regions, although the magnitudes outside of the regions HR1, HR2, ART1, ART2, ART3 are much smaller than those inside these regions and can be considered part of the noise signal.

It is noted in FIG. 3 (and related spectrogram FIGS. 5 and 6) that the Fourier coefficient magnitudes within the envelope curves C1, C1 contain the peak values and values around the peaks. It is understood that there are additional smaller valued Fourier coefficient magnitude points between each major region shown. That is there are smaller Fourier coefficient magnitude points between ART1 and HR1, and between HR1 and ART2, etc. These smaller Fourier coefficients magnitudes are shown for example in the projection of FIG. 4 and are typically part of or close to the noise signal.

Figure 4:
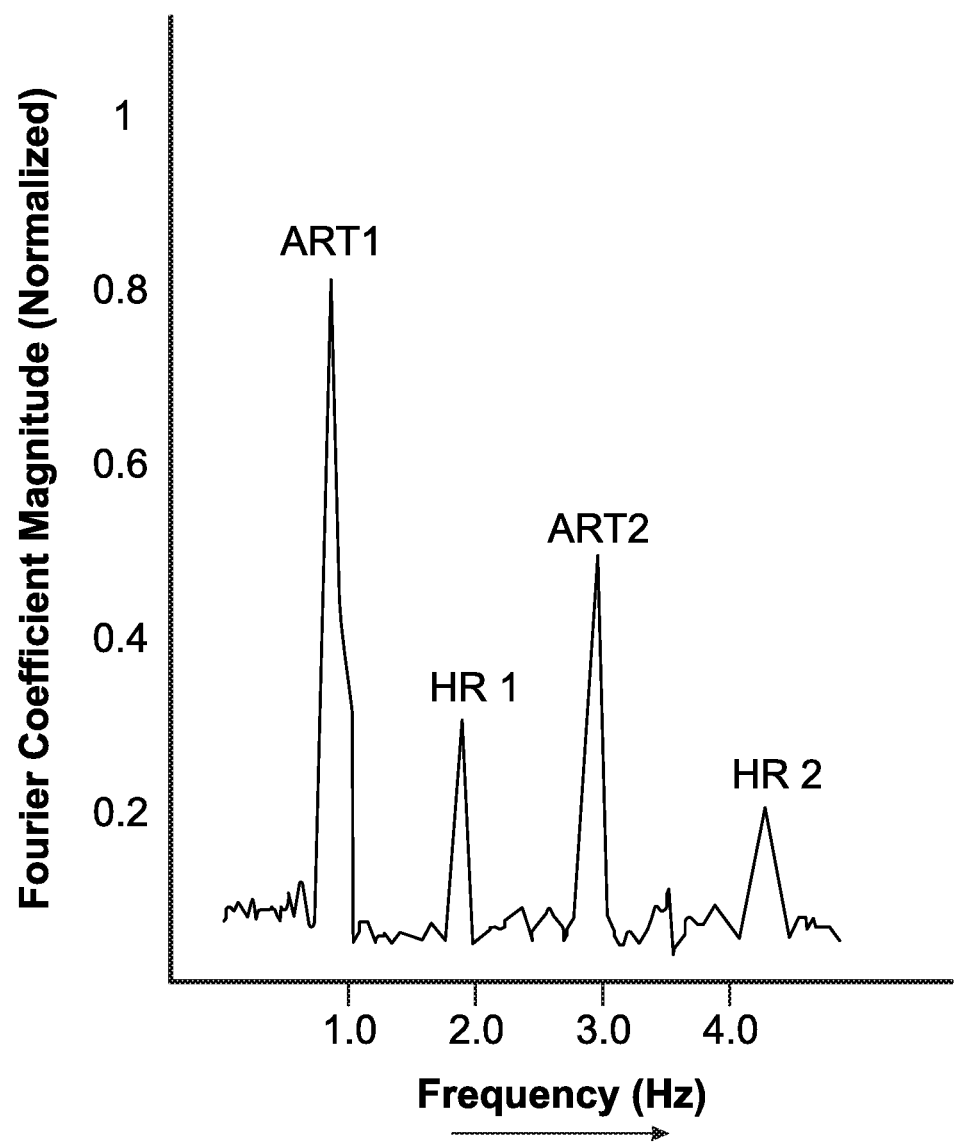
FIG. 4 is a two dimensional projection of the spectrogram of FIG. 3 onto the frequency axis showing both heart rate and artifact components according to various examples of the disclosure.

To better appreciate the 3-D nature of FIG. 3, an example 2-D projection of the FDHR signal magnitudes along the frequency (y) axis at the representative time tr is shown in FIG. 4. Thus, FIG. 4 plots the magnitude (normalized) of the Fourier coefficient on the y axis against frequency along the x axis. These magnitudes correspond to the size of the circles in the blowup portion of FIG. 3. Thus, the peak for HR1 is seen to have a frequency of about 1.8 Hz and have the highest magnitude of the spectrogram taken at representative time tr. The magnitude of the first harmonic HR2 peaks at about 4.2 Hz as seen from the HR2 region at representative time tr in FIG. 3 and as also shown in FIG. 4. The value of the peak at HR2 is much less than that of HR1. FIG. 4 also shows the artifact components at ART1 and ART2 corresponding to regions ART1 and ART2 of FIG. 3 at representative time tr. As in FIG. 3, it may be seen that in FIG. 4 the acceleration artifact components of the spectrogram are well separated from the true heart rate components.

Acceleration Artifacts as Measured by Accelerometer

Figure 5:
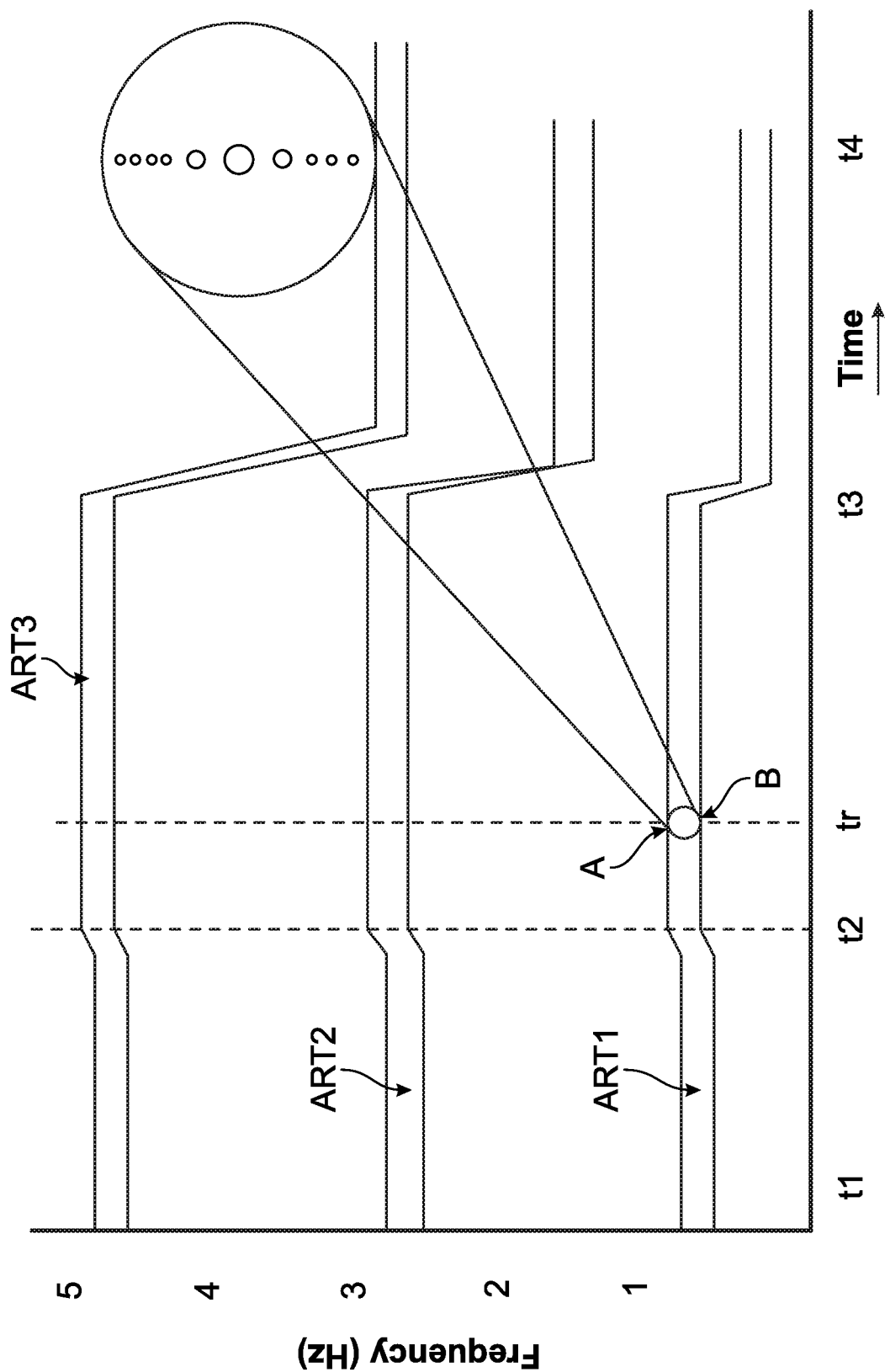
FIG. 5 is a three dimensional illustration of the acceleration spectrogram showing acceleration artifacts as measured by an accelerometer according to various examples of the disclosure.

FIG. 5 shows the 3-D plot of example accelerometer FDA signal magnitudes output from the spectrogram computation unit 34. These spectrograms can result from the output of the accelerometer 6. In FIG. 5, ART1 is the fundamental, ART2 is the first harmonic and ART3 is the second harmonic. In some examples, the second and higher order harmonics can be ignored. The ART1, ART2, ART3 regions of FIG. 5 correspond to the ART1, ART2, ART3 regions of FIG. 3. In FIG. 5, there are no heart rate components as the spectrograms of FIG. 5 results from signals taken only from the accelerometer. The blowup of FIG. 5 is similar to that of FIG. 3 in that it is meant to show the 3-D aspect of FIG. 5 and also the fact that the spectrogram peaks falls at approximately the central portion of the region ART1 at representative time tr. As in FIG. 3, spectrogram points can exist both within and outside of the regions ART1, ART2, ART3. Points A and B are labeled in FIG. 5 and are used below to explain how artifact compensation is performed in accordance with certain examples.

HR Fourier Coefficient Magnitudes Compensated for Acceleration Artifacts

Figure 6:
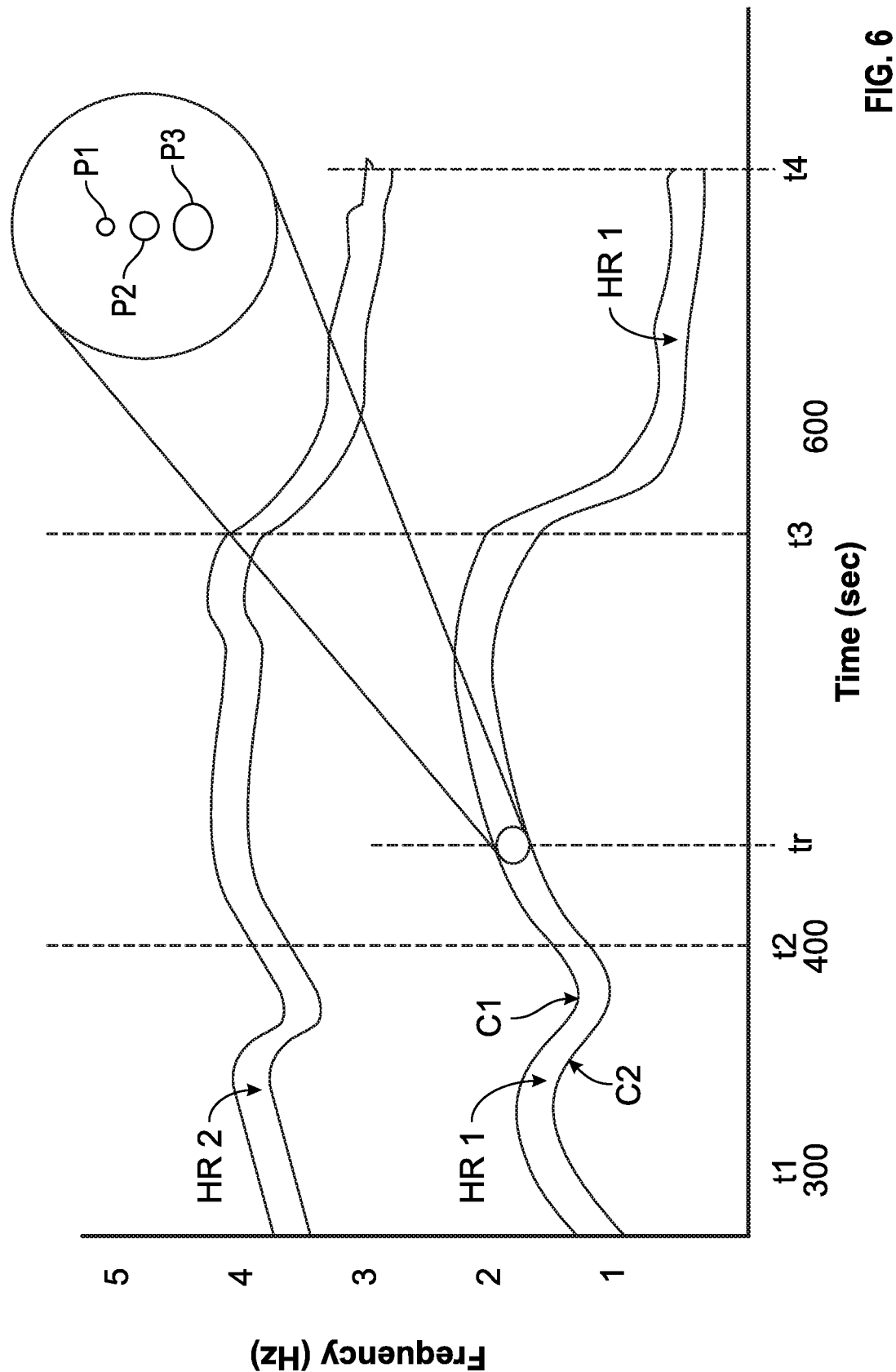
FIG. 6 is a three dimensional illustration of the heart rate spectrogram after compensation for the acceleration artifacts of FIG. 5 according to various examples of the disclosure.

FIG. 6 illustrates example compensated FDHR component magnitudes. That is FIG. 6 is the spectrogram of FIG. 3 after being compensated for by the acceleration compensation unit 36. The artifacts ART1, ART2 etc. can be readily identified from FIG. 5, and having been so identified, the compensation for the identified regions ART1, ART2 can be applied to FIG. 3 to result in FIG. 6. Although FIG. 6 does not show any defined artifact regions (such as ART1, ART2), the points corresponding to these regions are generally non-zero and can be close to noise levels and as such are not expressly shown in FIG. 6. (In this connection, it is noted that FIG. 3 also does not expressly show regions of noise, but generally in FIGS. 3 and 6 there will be non-zero Fourier coefficient magnitude noise values all along each representative time sample tr as shown in FIG. 4). In effect, the Fourier coefficient magnitudes for the artifacts has been reduced to such an extent that these magnitudes are comparable to the noise levels and are thus not expressly shown in FIG. 6.

The blowup portion of FIG. 6 shows three labeled points P1, P2 and P3. The three points are used in the subsequent description of the reward/penalty algorithm or methodology as describe in detail below in connection with FIGS. 9A-9C, 10A-10C and 11.

In accordance with examples, the FFT coefficients of each peak point and surrounding peak points of the artifact components ART1, ART2 can be replaced by interpolated values based on the coefficient values on either side of the peak. The peaks may be identified by requiring the ART1, ART2 etc. to exceed a predetermined threshold. The points on either side of the peak can be selected by taking the first local minimum on either side of the artifact peak. For ART1, the first local minimum on either side of the peak at representative time tr is represented by points A and B of FIG. 5. This interpolation is explained in more detail below.

Artifact Compensation

Figure 7:
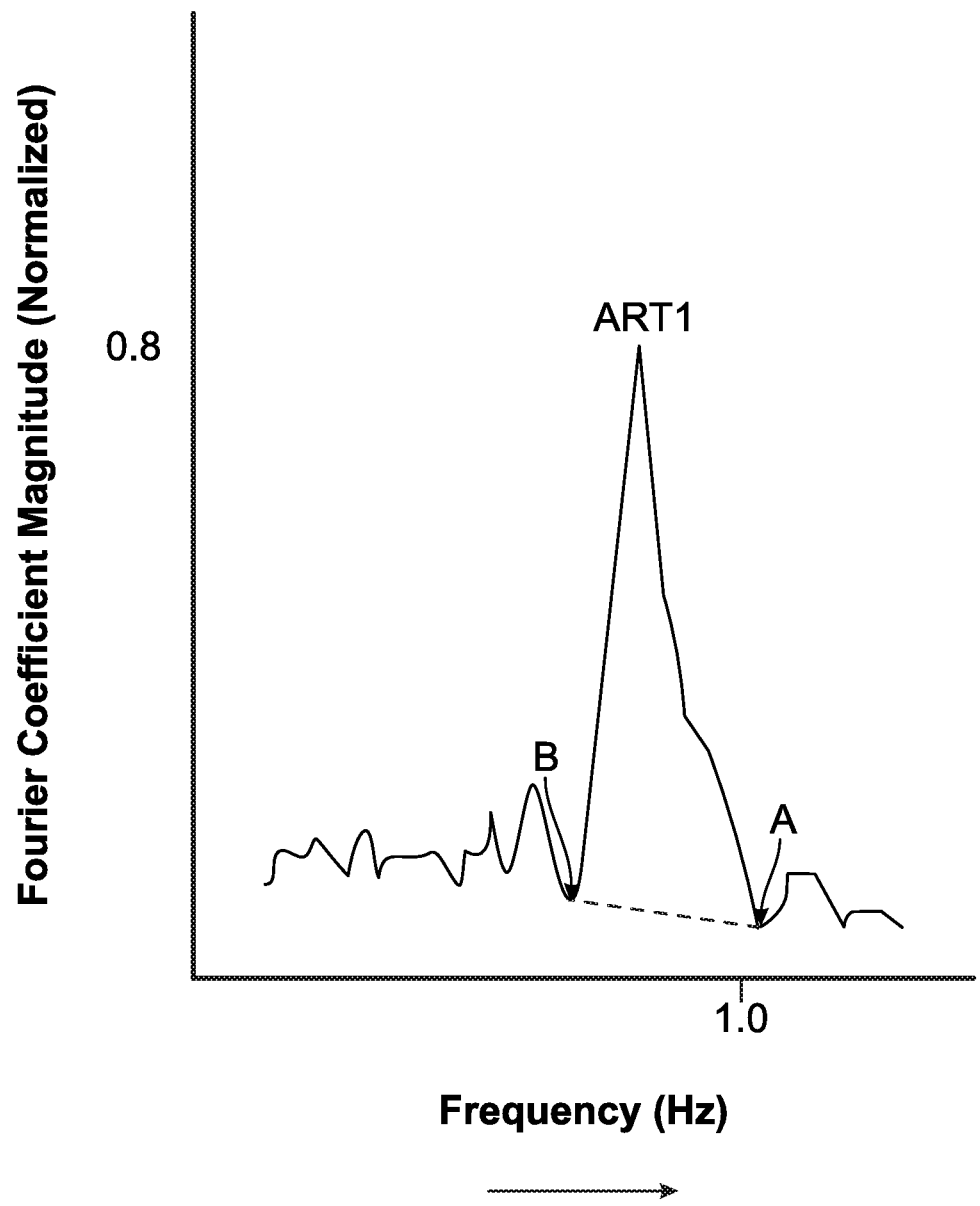
FIG. 7 is a graph showing an acceleration artifact peak and is used in describing various artifact compensations methods in accordance with various examples of the disclosure.

Artifact compensation may be understood in reference to FIGS. 4, 5, 7 and 8. FIG. 7 shows an example projection of FDA signal magnitudes of the ART1 region onto the y or frequency axis at the representative time tr. Similar to the projection of FIG. 4, FIG. 7 projects the 3-D representation of region ART1 of FIG. 5 into a 2-D representation at time tr. With reference to FIG. 7, point A can be located at the first local minimum to the right of the ART1 peak (toward the higher frequency direction) and while point B can be located at the first local minimum to the left of the ART1 peak (toward the lower frequency direction). In accordance with certain examples, one may interpolate between points A and B by taking a mean or average value between the two points, and then replace all points between A and B with the mean or average value. In other examples, interpolation can be done by drawing a straight line between points A and B as shown by the dotted line in FIG. 7 and using values along this line to replace the values of the ART1 peak. The result of such replacement is that the peak and surrounding points in the ART1 region (and all ART harmonic regions) is replaced with non-zero values thus effectively compensating for the acceleration artifacts in the frequency domain PPG signals.

Of course, the method of replacing the artifact peak for ART1 as described above can be performed for all artifact peaks (ART1, ART2, ART3 etc.) and for all times (e.g., every second) during which data is processed in the acceleration compensation unit 36.

Figure 8:
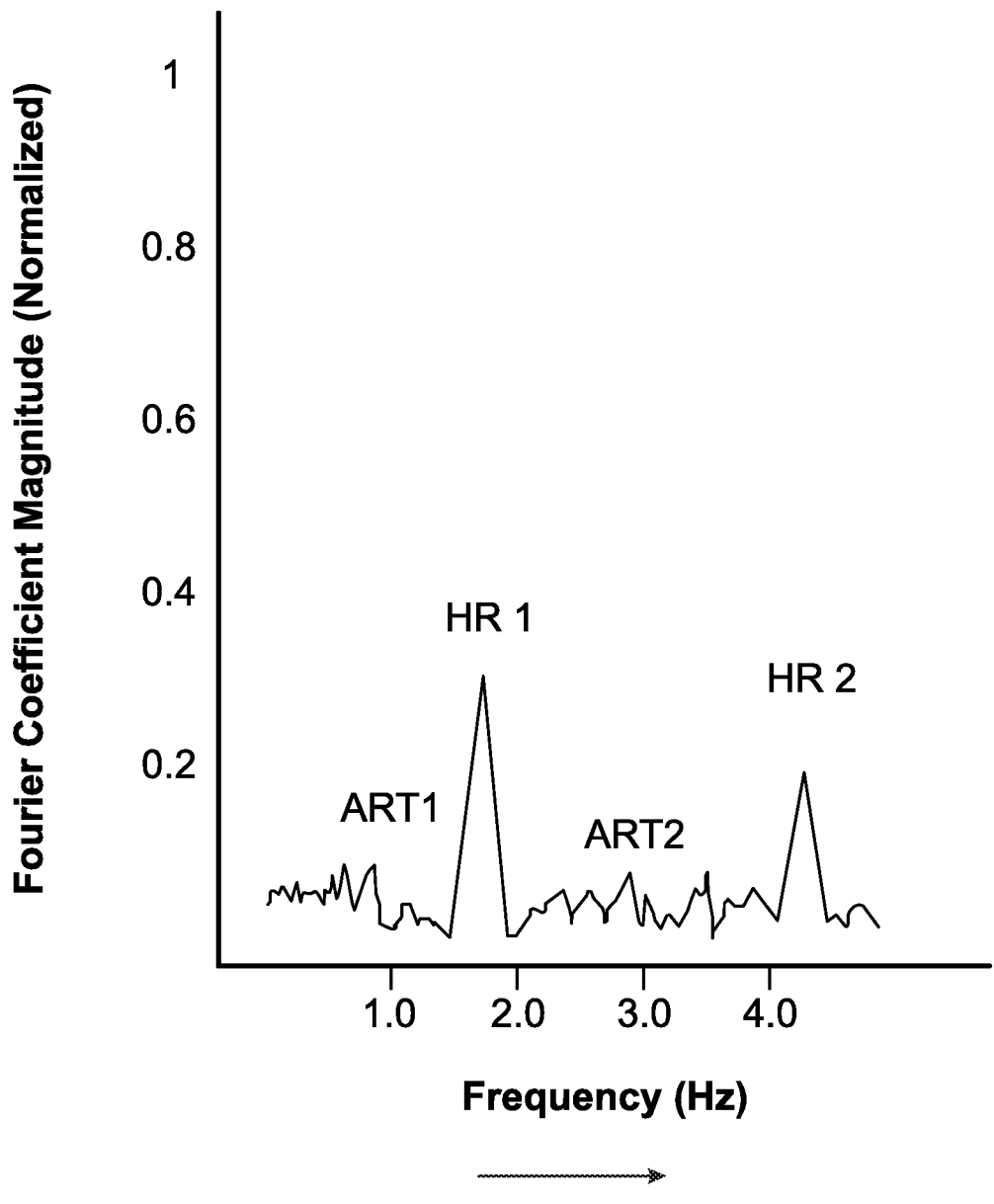
FIG. 8 is a graph similar to FIG. 4 but shows the application of the artifact compensation techniques in accordance with various examples of the disclosure.

After artifact compensation, the spectrogram can take the form as illustrated in FIG. 8. FIG. 8 is similar to FIG. 4, but now the acceleration induced artifacts have been compensated for, such as by being reduced in magnitude, such that their influence on the coefficient magnitudes of the HR fundamental and HR harmonic peaks are substantially reduced or minimized. FIG. 8 may also be understood at the 2-D projection of the spectrogram of FIG. 6 at representative time tr onto the frequency axis (y axis). The relationship of FIG. 8 to FIG. 6 is the same as the relationship of FIG. 4 is to FIG. 3.

It will be apparent that other methods may readily be apparent to those of skill in the art to compensate for the unwanted artifact signals ART1, ART2 etc. so that only the true heart rate signals regions HR1, HR2 etc. remain.

In the event that the artifact region is non-periodic, there will be no harmonics and in this case only the single artifact peak is compensated.

One function of the post-processing unit 38 of FIG. 2 is to apply one or more post-processing procedures to the output of the acceleration compensation unit 36.

Harmonic Boost

A first post-processing process can provide for a "harmonic boost" which is the augmentation of the fundamental HR1 peak by the addition thereto of a first harmonic HRT2 peak and optionally by higher harmonics if desired. In some examples, a Gaussian convolution of the spectrogram of FIG. 8 can be taken before the HRT2 peak values are added to the HR1 peak values. Thus, the harmonic boost can be performed by first convolving the entire spectrogram of FIG. 8 (containing the peaks for HR1 and HR2) for each time sample (such as representative time sample tr in FIG. 6) with a Gaussian kernel and for each Fourier coefficient magnitude data point at frequency f (for the points within the peak of HR1) adding thereto the Fourier coefficient magnitudes at frequency 2f. In other words, the points of the peak of HR2 can be added to the points of the peak of HR1 so that the new values of the points of the peak at HR1 can be "boosted" by the addition thereto of the higher harmonic points (the points at twice the frequency for each point).

The convolution of the spectrogram of FIG. 8 with the Gaussian kernel serves to provide a low pass filtering of the spectrogram. Further the Gaussian kernel convolution produces a weighted average of the points being convolved. Thus, the higher value points in the HR1 and HR2 peaks can be given more weight and the lower value points less weight. This can have the effect of enhancing the highest values of the peak points so that the peaks themselves are more readily defined.

Peak Boost

As a further post processing step, the peak values of the harmonic regions HR1 and HR2 may be further boosted. The peak boost process can involve identifying each local maxima in the projected frequency 2-D plot (FIG. 8) and multiplying each peak by a factor greater than one (e.g. by 1.2). This can have the effect of enhancing the peak values. Only the largest single value within each region HR1, HR2 (corresponding to the peak point) may be multiplied. This boost can further enhance the peak value by providing even further definition of the peak value within HR1, the region of most interest.

In the post processing unit 38 the post processing steps of harmonic boost and peak boost may be performed individually without the other being performed at all or both harmonic boost and peak boost may be performed in either order. In some examples, both harmonic boost and peak boost can be performed.

Reward/Penalty Methodology

Figures 9A, 10A:
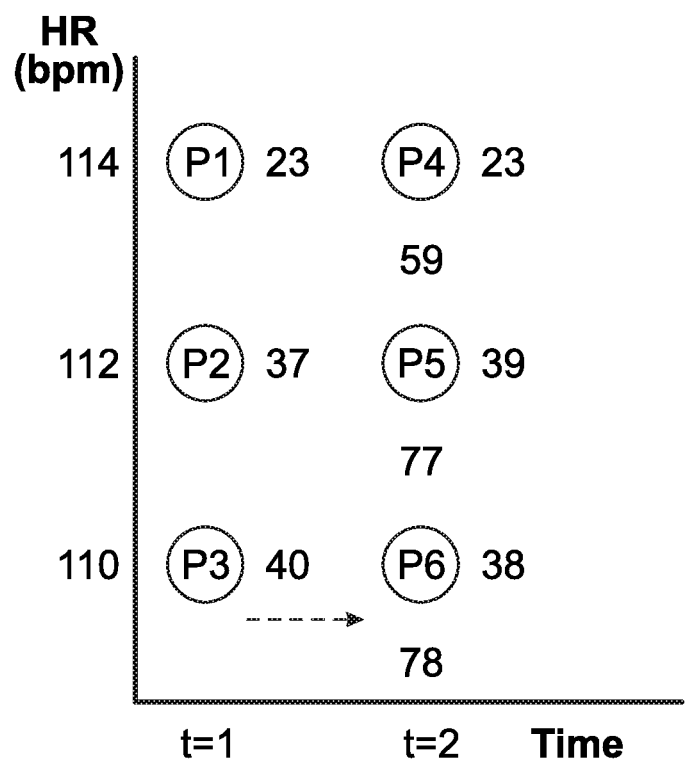
FIG. 9A illustrates a heart rate (HR) path optimization algorithm using 6 points according to various examples of the disclosure.
FIG. 10A shows a summary of path lengths for the six point path optimization algorithm of FIG. 9A according to various examples of the disclosure.
Figures 9B, 10B:
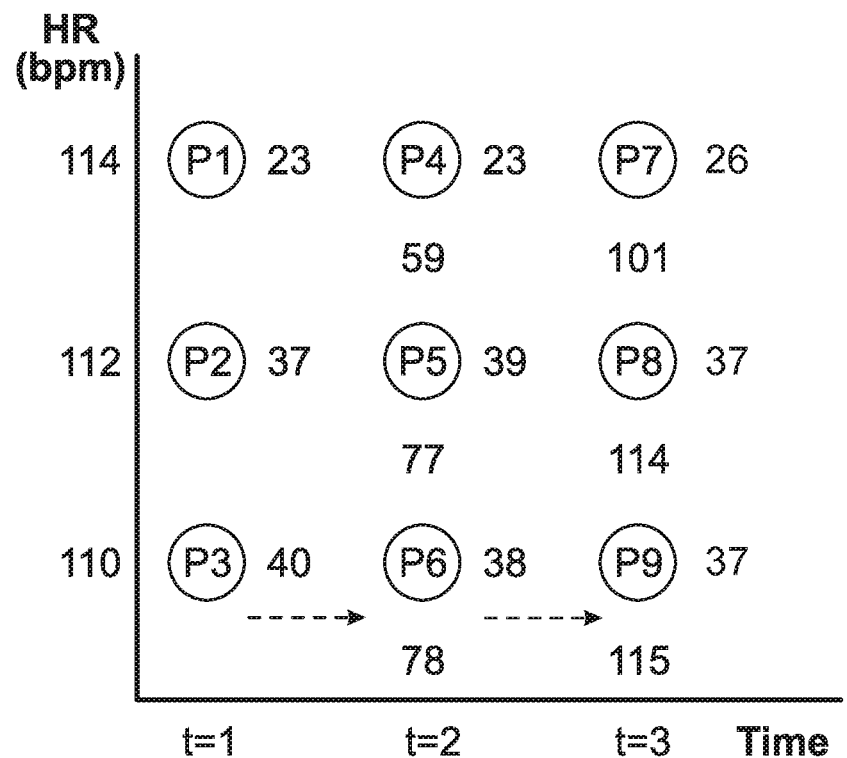
FIG. 9B illustrates the HR path optimization algorithm using six points according to various examples of the disclosure.
FIG. 10B shows a summary of path lengths for the nine point path optimization algorithm of FIG. 9B according to various examples of the disclosure.
Figures 9C, 10C, 11:
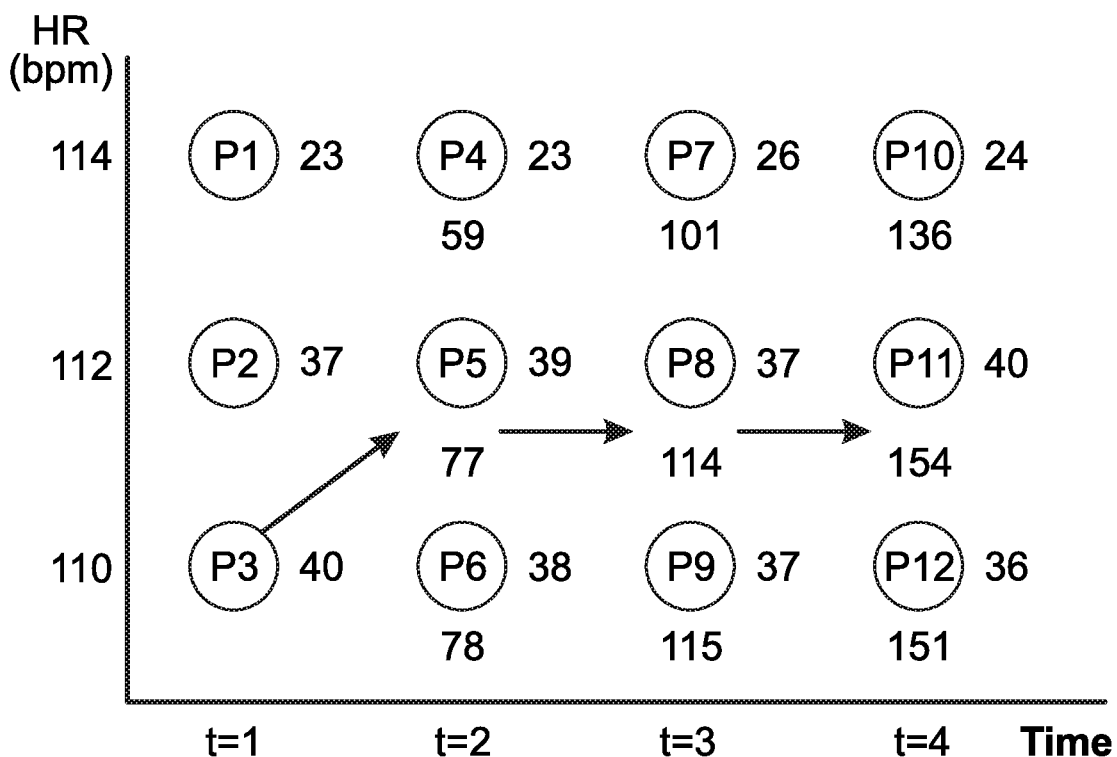
FIG. 9C illustrates the HR path optimization algorithm using 12 points according to various examples of the disclosure.
FIG. 10C shows summary of path lengths for the 12 point path optimization algorithm of FIG. 9C according to various examples of the disclosure.
FIG. 11 shows correspondence table for determining the total path using previously determined optimum candidate paths according to various examples of the disclosure.

FIGS. 9A-9C, 10A-10C and 11 illustrate an exampler operation of the path optimization unit 40 of FIG. 2. FIGS. 9A-9C are simplified, high level depictions of the spectrogram of FIG. 6 at a particular time sample (such as representative time tr) after any desired post processing by post processing unit 38. FIG. 9A shows thee points at time t=1, labeled P1, P2 and P3, and three points at time t=2 labeled P4, P5 and P6. Points P1, P2 and P3 of FIG. 9A correspond to points P1, P2 and P3 respectively of the blowup portion of FIG. 6. Points P4, P5 and P6 would correspond to another set of three points at a spectrogram time sample of tr+1. Thus, FIGS. 9A, 9B and 9C equate directly to a simplified version of FIG. 6 but in the case of FIGS. 9A, 9B and 9C the y axis is labeled with heart rate values in beats per minute (bpm) as opposed to frequency in Hz. Further, in FIGS. 9A-9C, there are only three choices of heart rate values on the y axis, namely, 110, 112 and 114. Again, this is done for convenience of explanation.

As seen in the example of FIG. 9A, Point P1 has a Fourier coefficient magnitude of 23; P2 a magnitude of 37 and P3 a magnitude of 40. These three magnitudes are normalized to 100 for the sake of convenience and illustration. Normalization can take place at each of the spectrogram sample times. In each of the FIGS. 9A-9C, the values shown adjacent and to the right of the points along any time line t=1, t=2, etc. represent the Fourier magnitudes at these points. The points are representations of a portion of the HR1 region of the spectrogram of FIG. 6. These magnitudes are the absolute value (complex conjugate) of the Fourier coefficients, and they can correspond to the probability associated with that coefficient. Thus, in reference to FIG. 9A, point P3 has a 40% chance of representing the spectrogram peak; P2 at 37% chance and P1 a 23% chance. In terms of heart rate, this means that there is a 40% probability that the heart rate at time t1 is 110 beats per minute (corresponding to the y value associated with point P3); a 37% probability that the heart rate is 112 bpm (corresponding to the y value associated with point P2); and a 23% probability that the heart rate is 114 bpm (corresponding to the y value associated with point P1). It may thus be seen that the Fourier coefficient magnitudes at each sampling time can correspond to the relative probability of the peak existing at that point and consequently, a most probable path can be based at least in part on a path that takes into account these highest probability consecutive points.

The objective is to find the point at each sampling time that is the most probable and thus most optimally representative of the true heart rate at each sampling time (e.g., each second or each fixed time interval). Hand in hand with the determination of the most probable point (heart rate) at each time, is to find the most optimum path during all times within the time interval under consideration. That is, a goal may be to find the heart rate optimum path (e.g., the most probable or optimum value of the heart rate over time), for example, during an exercise period and to be able to provide an output indicative of this optimum path. In this way, the user doing an exercise routine may be able to see a an output such as a time graph or chart of his/her heart rate at each time interval (one second, five seconds etc.) during the just completed or in progress exercise routine. It is pointed out as will be seen below, that the determination of a particular point as having the highest Fourier coefficient magnitude for a given sampling time may not mean that such a point is ultimately part of the overall most probable heart rate path, and it is necessary to maintain a knowledge of earlier best heart rate paths as time goes on since the optimal path is dynamically determined at each sampling time and can also be determined based on the Fourier coefficients in the current and past samplings.

In practice, instead of three points at each time interval (e.g., one second), there may typically be on the order of 210 such points, for example, representing a possible range of HR from about 30 to about 240 bpm. That is the y axis may typically span the range of 30-240 beats per minute.

The algorithm utilized in the path optimization is termed the reward/penalty algorithm and is configured such that a candidate path can be given a reward for all points the optimum path passes through, and a penalty can be assessed based on the distances between points. By distance between points it is intended to mean the vertical distance (y direction or heart rate distances as in FIGS. 9A-9C). In FIGS. 9A-9C and 10A-10C and 11, when the candidate path passes through two points the Fourier coefficients of those two points can be added together. Thus, in the example of FIG. 9A, a candidate path going from path P2 to P5 would have a value of 37+39=76 as seen in FIG. 10A at the intersection of P5-P2. However, in going from point P2 to P4, (a one unit vertical jump in this case equal to two bpm), a penalty can be imposed by subtracting a value of "2" from the added coefficients. Thus, the path "length" in going from P2 to P4 is 37+23−2=58 again as shown in FIG. 10A. The penalty in going two vertical jumps (y direction of 4 bpm) is −4 so that the "length" in going from P3 to P4 would be 40+23−4=59. In general, the penalty can be increase as the vertical distance between sampling points increases, and the penalty can be subtracted from the path length giving it a lower overall score. This increase in penalty may be understood in that it may not be probable for the heart rate to drastically change from one sampling time (e.g., one second) to the next. The larger the change from one second to the next, the smaller is the probability of such a change. The optimum path selection algorithm can take this into account by imposing the above described penalties. This penalty can assure that a non-smooth path is less likely than a smooth path. In general, the penalty can increase with increasing vertical distances. A constant, determined experimentally, may be employed as a multiple in a $2^{nd}$ order polynomial to calculate the penalty. Thus if the constant is 1, a vertical jump of 1, 2 and 3 (corresponding in FIGS. 9A-9C to a jump of 2, 4 and 6 beats per minute) would correspond to a penalty of −2, −4, −9. While the example of FIGS. 9A-9C show a vertical jump to be two bps, the vertical jump (threshold) triggering the penalty may be selected to be otherwise and may be chosen to be any fixed number of beats per minute typically between 2-10 and preferably 5. Thus, if five bps is chosen as the penalty threshold, there would be no penalty for heart rate changes (the vertical jumps above) between successive sampling times of 4 bpm or less; and a penalty (e.g., −2) for a heart rate change of 5 pbm (or between 5-9 bpm); a −4 penalty for a two jump heart rate change of 10 bpm (or between 10-14) and −9 penalty for a three jump heart rate change of 15 bpm (between 15-19) and so forth.

Flowcharts showing an exemplary algorithm for computing the optimum path (computed in the path optimization unit 40) are shown in FIGS. 12-15, and these flowcharts will be used in conjunction with FIGS. 9A-9C, 10A-10C and 11. It is noted that according to some examples the flowcharts can represent the program flow of a programmable computing device implemented to carry out the functions of the path optimization unit 40. This programmable computing device can also be programmed to carry out the functions of one or more of the remaining units 30, 32, 34, 36, and 38 of FIG. 2.

Figure 12:
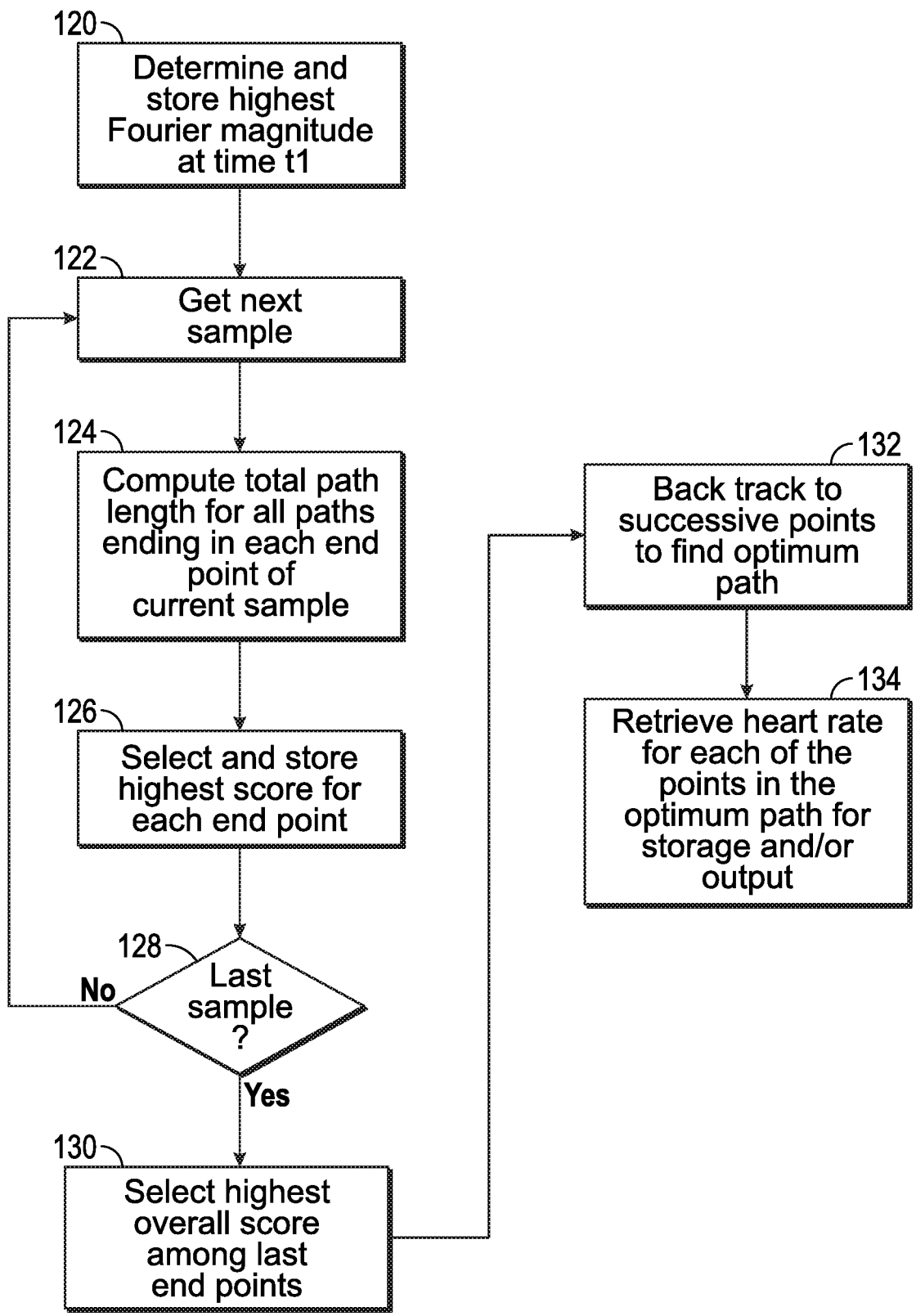
FIG. 12 is a flowchart showing program steps for determining and outputting the heart rate and the determined optimum path at the end of an exercise time period according to various examples of the disclosure.

One may initially assume, as per step 120 of FIG. 12, that the largest Fourier transform coefficient at time t1 corresponds to the most probable heart rate at time t1. Thus, at time t1, a heart rate of 110 (corresponding to the highest Fourier coefficient magnitude of 40) would be the most probable. However, in accordance with certain examples, the heart rate value can be recomputed after additional coefficients at additional times are considered as well. In accordance with certain examples, the HR value can be is recomputed for each new sampling time period, that is, for example, for each second as new Fourier coefficients are calculated and output from the post-processing unit 38.

At time t=2, a second set of Fourier coefficient magnitudes can be obtained as shown in step 122 of FIG. 12. For each sample point P4-P6, the path value (sometimes called the path "length") can be computed utilizing the sum of Fourier coefficient magnitudes minus the penalties (as a function of vertical jumps) as explained above and as indicated in step 124 of FIG. 12. These results are shown in the examples of FIG. 10A. As seen in FIG. 10A, the path length can be computed for all points ending in point P4. There are three such paths starting from Pb, P2 and P3. The path length P1-P4 is 23+23=46. The path length P2-P4 is 37+23-2 (penalty)=58. The path length P3-P4 is 40+23−4=59. The same procedure can be performed for all paths ending at point P5. The P1-P5 path length is 23+39−2=60; the P2-P5 path length is 37+39=76; the P3-P5 path length is 40+39−2=77. For the final paths ending in point P6 one has path length P1-P6 of 23+38−4=57; path length P2-P6 of 37+38−2=73; and path length P3-P6=40+38=78. In accordance with step 126 of FIG. 12, the highest score (path length) can be selected and stored for each end point. Thus, score 78 can be selected and recorded as the highest score (path length) ending at P6. It originates from P3. Likewise the highest score path ending in P5 originates from P3 and the highest score path ending at P4 also originates from P3. In FIG. 10A, these highest scores are shown circled. In some examples, after these highest score paths have been determined, it is not necessary to store the losing score paths. That at point P6 it may only be necessary to know that the most optimal path ending at P6 originates from P3.

Considering time t=2, it may be seen that the highest scoring path is the one from P3 to P6. This path is shown in the dotted line of FIG. 9A. It is noted that this path corresponds to a heart rate value of 110 at time t=2, the same as that at time t=1. This determination at time t=2 can be made even though the value of the Fourier coefficient magnitude at point P5, corresponding to a heart rate value of 112, is actually higher than the value of the Fourier coefficient magnitude at point P6, corresponding to the value of 110. In this example, it may thus be seen that the optimum heart rate is determined not just in view of the most recent spectrogram samples of the Fourier coefficient magnitudes but also in view of the previous spectrogram samples.

As seen in the example of FIG. 10A, the highest scores 59, 77 and 78 are shown below each of the points P4-P6 respectively. In this example, the losing scores need not be further considered.

At step 128 in FIG. 12 it can be determined whether this current data sample (Fourier coefficient spectrogram data) is the last to be analyzed. If there is more data, as for example, if the exercise period of the user is still in progress so that more data is coming into the device 12, then the program flow returns to step 122 to get the next sample, here the sample at time sampling point t=3.

FIG. 9B shows the continuation of the optimum path algorithm for the next three data points at time t=3. Here points P7-P9 are contained in the next sampling time having Fourier coefficient magnitudes of 26, 37 and 37 respectively. Again, these values are normalized to 100. Again in accordance with step 124 of FIG. 12 the path length can be computed for all paths ending in each of the three new data points P7, P8 and P9. For paths ending at point P7, the path values (path length) from P4-P7 is 59+26=85. It is noted that the value 59 is used here instead of the value 23 since it is the total path length that is desired to be calculated and the value "23" was already considered in determining the path length leading to point P4 from the originating highest value path P3-P4 per FIG. 10A. Thus, the path lengths ending in P7 are P4-P7=85; P5-P7 calculated as 77+26−2=101 (−2 being the penalty) and P6-P7 calculated as 78+26−4=100 (−4 being the penalty).

In a similar fashion the path lengths may be calculated per step 124 of FIG. 12, and the results are shown in FIG. 10B with paths ending at P8 being P4-P8 calculated as 59+37−2=94; P5-P8 calculated as 77+37=114; and P6-P8 calculated as 78+37−2=113. For paths ending at point P9 the results are P4-P9 calculated as 59+37−4=92 (with −4 penalty); P5-P9 calculated as 77+37−2=112 (with −2 penalty) and P6-P9 calculated as 78+37=115. The results are shown in FIG. 10B with the circled values representing the most optimum paths at time t=3. Again, the highest scores 101, 114, and 115 are shown below their respective points P7, P8 and P9.

Considering time t=3, it may be seen that the highest scoring path is the one from P6 to P9. This path is shown in the dotted line of FIG. 9B. FIG. 9B also shows the highest scoring or most optimum path ending at point P6 which, as in FIG. 9A, is the one originating from point P3. Thus, FIG. 9B shows the optimum path at time t=3 to be the path P3-P6-P9. This path would correspond to heart rate value of 110 at each sampling time t=1, 2, 3.

At step 128 of FIG. 12 it can be determined again if additional spectrogram samples are to be considered. Here it can be assumed that there is one more sample at time t=4 which is to be considered as shown in FIG. 9C. Thus the program once again cycles to step 122 to obtain the next data samples.

The t=4 time sample includes spectrogram data points P10, P11 and P12 with Fourier coefficient magnitudes of 24, 40 and 36 respectively. Again, in accordance with step 124, the total path length or value can be computed for all paths ending in the three end points P10, P1l and P12.

For paths ending at P10, path length values for P7-P10 can be calculated as 101+24=125; path length values for P8-P10 can be calculated as 114+24−2=136 (−2 penalty); and path length values for P9-P10 can be calculated as 115+24−4=135. For paths ending at P11, path length values for P7-P11 can be calculated as 101+40−2=139 (−2 penalty); path length values for P8-P11 can be calculated as 114+40=154; and path length values for P9-P11 can be calculated as 115+40−2=153 (−2 penalty). Finally, for paths ending at P12, path length values for P7-P12 can be calculated as 101+36−4=133 (−4 penalty); path length values for P8-P12 can be calculated as 114+36−2=148 (−2 penalty); and path length values for P9-P12 can be calculated as 115+36=151. Again, the highest value for the three candidate paths ending at each point P10, P11 and P12 is circled in FIG. 10C, and these scores are placed below their respective points P10, P11 and P12 in FIG. 9C.

Proceeding now to step 126 of FIG. 12, the highest score of each of the end points P10, P11 and P12 can be selected and stored. These points are just the circled points in FIG. 10C. Assuming now that there are no more data sample points (spectrogram) to be considered (e.g., the exercise program of the user has completed), the decision in step 128 of FIG. 12 is made as "yes" and the program proceeds to step 130 where the overall highest score is selected among the most recently analyzed end points, that is amongst points P10, P11 and P12. It may be seen that the highest score is 154 which ends at point P11. This score of 154 indicates that at time t=4 the most probable value of the heart rate is 112 as this heart rate value is the y coordinate associated with point P11.

Thus, point P11 can be determined to have the highest overall path length score and consequently corresponds to the most probable heart rate value associated with this point. The program next proceeds to step 132 in FIG. 12 where the optimum path can be determined. This path can be determined by back-tracking from the highest scoring point at time t=4 to the highest scoring path which ended at this point P11. From the table of FIG. 10C it may be seen that of the points ending at P11, point P8 had the highest score meaning that the path P8-P11 was the most probable path from among the paths feeding point P11.

Now considering the point P8 as the ending point, the table in FIG. 10B can be utilized to determine that the path from P5 to P8 gives the highest scoring path from among all of the paths feeding to path P8. Thus, the path so far is P5-P8-P11. Back tracking one final time to t=1, it can be determined from the table in FIG. 10A that the highest scoring path from among all the points feeding into point P5 is that originating from path P3. Thus, the complete path calculated at time t=4 is P3-P5-P8-P11 as shown by the solid line in FIG. 9C.

Instead of storing all of the path scores at a given time terminating a each ending point and originating at each possible starting point, in some examples the most probable path can be kept by considering just the points at the time under consideration (current time) and the points immediately preceding the time under consideration. Thus, instead of storing all values in FIGS. 10A, 10B and 10C, just the points having the highest path value can be stored. Thus, FIG. 11 shows that for current point P11 the previous point (having the highest score to this ending point) is P8. Similarly, if the current point is P8, the previous point (having the highest score to this ending point) is P5. From P5 the previous point is P3. The total path is then P3-P5-P8-P11. In fact, FIG. 11 is a distilled composite of FIGS. 10A, 10B and 10C showing only the data that may be relevant in determining the optimum path. Thus according to examples of the disclosure is generally not necessary to keep track of the "losing" scores; that is, for paths ending at point P5 it is not necessary to keep track of the paths P1-P5 and P2-P5. Only the point associated with the highest scoring path at each sampling time (t=1, 2, 3, 4) needs be retained. Thus, for ending point P5 it is only necessary to know that the optimum path feeding this point (at the immediately preceding time sample) is coming from P3. As another example, for ending point P11 it is only necessary to know that the optimum path feeding this point (at the immediately preceding time sample) is coming from P8. In this fashion FIG. 11 shows a concise way to determine the optimum previous point feeding any given current point, and in using FIG. 11, it is possible to back-track to determine the entire optimum or most probable path.

Once the optimum path points have been identified using FIG. 11, the heart rate values associated with each of these points is retrieved for further storage and/or output in step 134 of FIG. 12. From the data of the highest scoring points taken from FIG. 11, and the original spectrogram data input into the path optimization unit 40, it may be determined that the heart rate corresponding to points P11, P8 and P5 (the y coordinate value of these points) is 112, and the heart rate associated with point P3 is 110. Thus, at times t=1 to t=4, the heart rate history is represented as 110, 112, 112, 112. In step 132 the program may store this heart rate history and/or output this history to an output device such as I/O unit 10 and or one or more of remote output unit 18 and touch screen 20. (See FIG. 1). Instead of or in addition to the heart rate history, only the final heart rate value may be output so that a user of the device may know the heart rate at the end of the exercise program. This heart rate data may also be stored for later retrieval and study by the user of the device.

In comparing FIGS. 9C and 9B it may be seen that the optimum path is dynamically changed as a result of new sampling data (spectrogram) introduced at time t=4 as compared to t=3. The optimum path changed from P3-P6-P9 (at time t=3) to P3-P5-P8-P11 (at t=4). This example shows why it can be important to keep in play the identification of the highest scoring points feeding into each ending point (FIG. 11). Maintaining this back-tracking data as per FIG. 11 can enable the dynamically determine of paths that are later found to be the optimum path and which replace candidate paths previously determined to be optimal.

Figure 13:
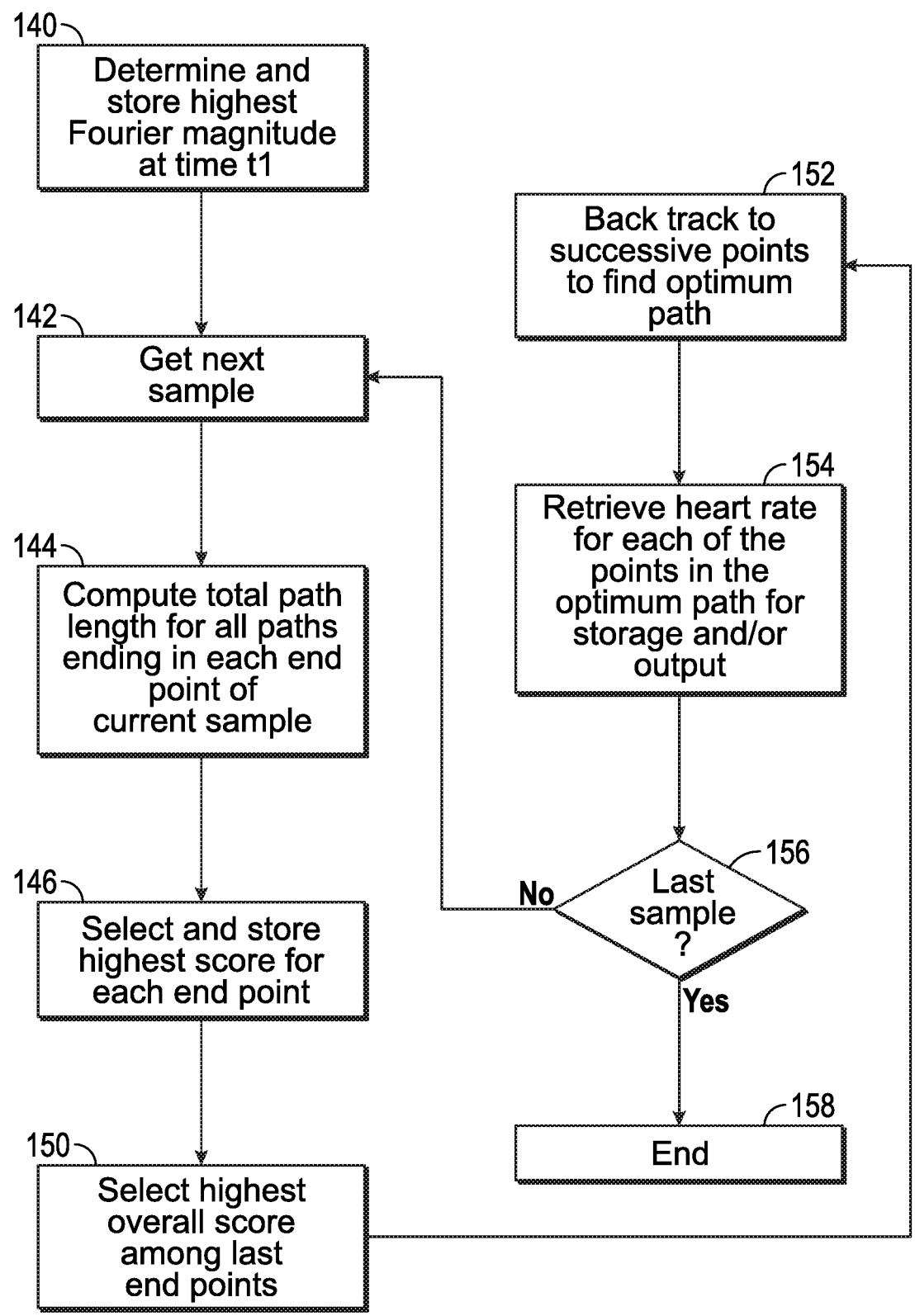
FIG. 13 is a flowchart showing program steps for determining and outputting the heart rate and the determined optimum path at each sampling time during an exercise time period according to various examples of the disclosure.

FIG. 13 is an example flowchart similar to that of FIG. 12, but shows the program flow assuming that the heart rate is to be displayed at each sampling time. In FIG. 13, steps 140, 142, 144, 146, 150, 152 and 154 are the same as steps 120, 122, 124, 126, 128, 130, 132 and 134 respectively of FIG. 12. Thus, in FIG. 13, at step 140, the highest Fourier coefficient magnitude can be determined at time t1 which would correspond to determining that P3 of FIG. 9A has the highest Fourier coefficient magnitude. In step 142, the next sample is taken corresponding to examining the points P4-P6 at time t=2 in FIG. 9A. In step 142 the total path length can be computed for all points ending in each end point of the current sample which corresponds to determining the path length (score) as shown and explained in FIG. 10A. In step 150 the highest of the computed scores can be determined corresponding to the circled end points shown in FIG. 10A. In step 152, back tracking to successive points can be performed to find the optimum path. For FIG. 9A, the back tracking can be simple and amounts to going back only one step to identify the optimum path P3-P6. For time t=4, the back tracking per FIGS. 9C and 11 would be such as to identify the path P3-P5-P8-P11. In step 154 the heart rate values can be retrieved for each of the points in the optimum path and these heart rate values can be stored and/or output. At step 156, it can be determined if there are any further sample from the post processing unit 38 (FIG. 1) and if so the program goes again to step 142 where another iteration of steps 144-154 can be performed. If in step 156 it is determined that the last sample has been processed, the program goes to end step 158. Thus, in FIG. 13, the heart rate values at each time sample may be displayed or output to the user and additionally, the optimum path data is also available and may be displayed or output to the user as well.

Figure 14:
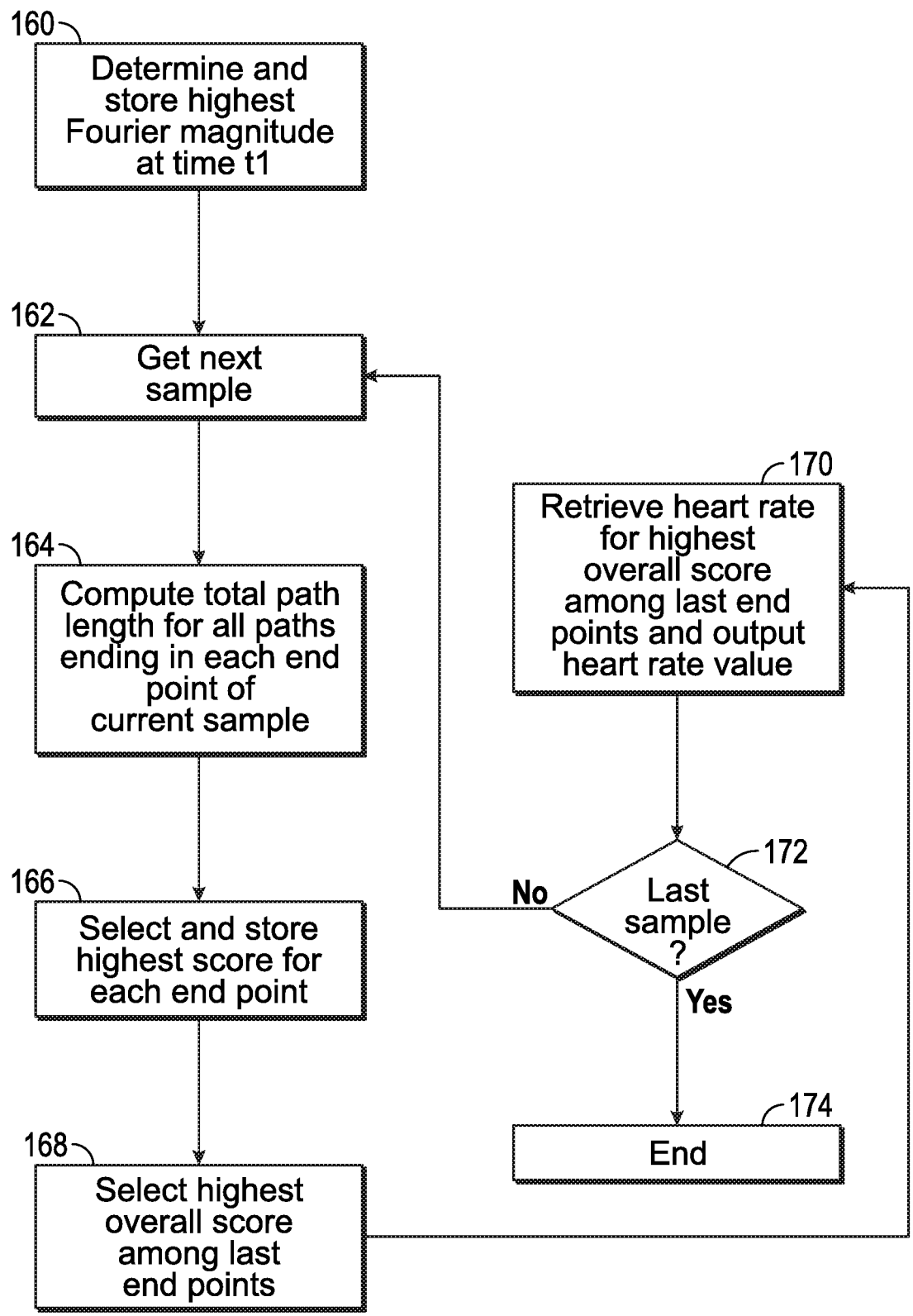
FIG. 14 is a flowchart showing program steps for determining and outputting the heart rate at each sampling time during an exercise time period according to various examples of the disclosure.

FIG. 14 is a flowchart similar to FIG. 13, but omits the step 152 found in FIG. 13. Thus, steps 160, 162, 164, 166, 168, 170, 172 and 174 of FIG. 14 are the same respectively as steps 140, 142, 144, 146, 150, 154, 156 and 158 of FIG. 13. The program of FIG. 14 can be useful to display the heart rate data to the user at each time sample, but does not provide output data for the optimum path. Thus, while the highest score of the Fourier coefficient magnitudes can be computed using the reward/penalty algorithm, this algorithm may now only be used to display or otherwise output to the user an indication of the computed heart rate at each sample time.

It is noted that the device 12 may be user configurable so that the user may select one of several program modes of operation corresponding to the flowcharts of FIGS. 12-14.

Figure 15:
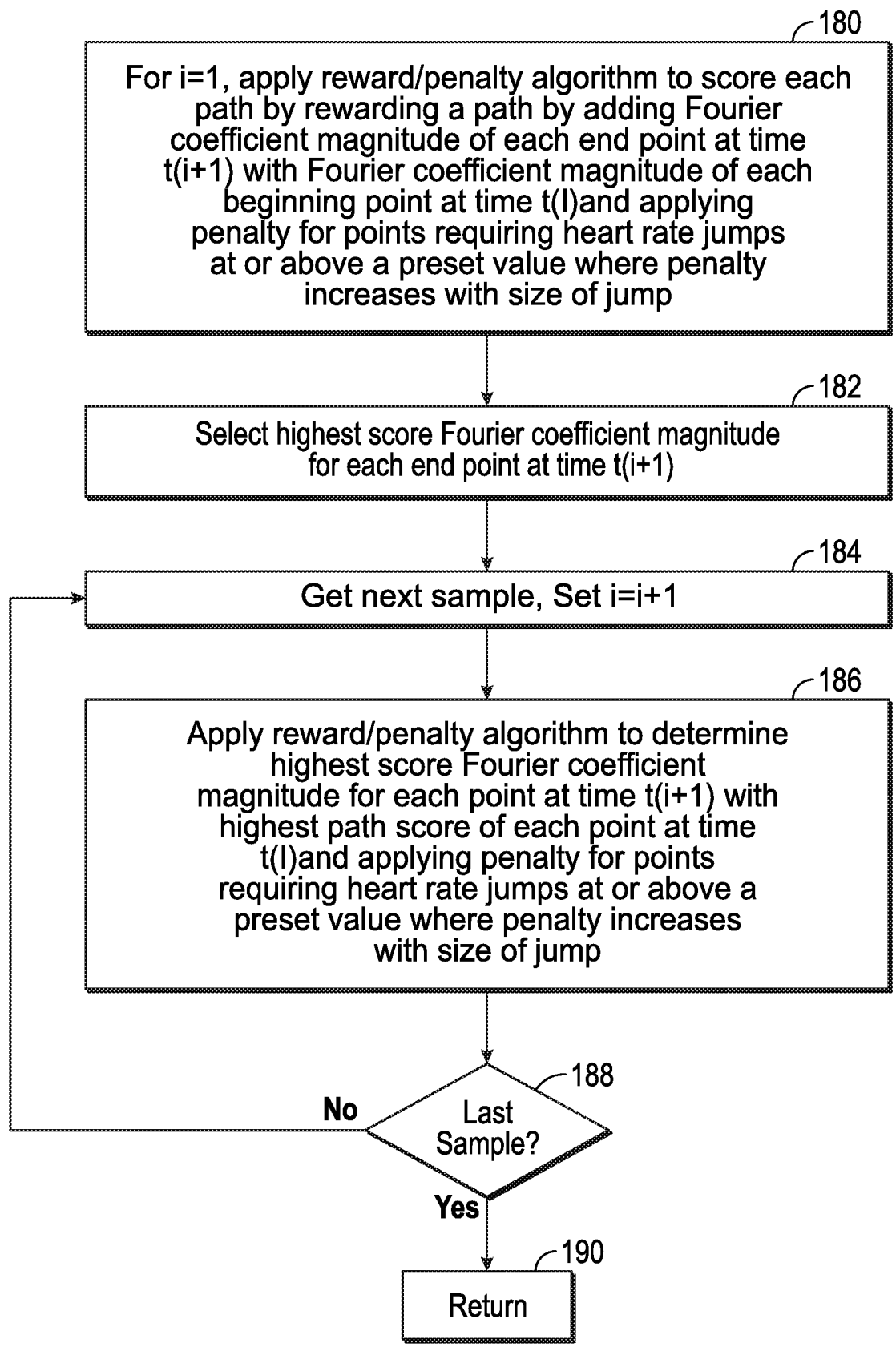
FIG. 15 is a flowchart showing details of the reward/penalty algorithm used in computing the heart rate path optimization according to various examples of the disclosure.

FIG. 15 shows in more detail an example reward/penalty algorithm and may be understood as a subroutine called from step 124 of FIG. 12, step 144 of FIG. 13 and step 164 of FIG. 14. In FIG. 15, step 180 can compute the path considering the initial two data samples (initial two spectrograms). Thus, i can be set to 1 and all paths to end points at time i=2 can be calculated. As an example, referring to FIGS. 9A and 10A, the path lengths ending at point P4 and originating from point P1 can be rewarded by adding together the Fourier coefficient magnitudes associated with P1 (23) and P4 (23). No penalty may be applied here since the P1-P4 path does not traverse a vertical distance, e.g., there are no jumps from HR of 110 to another HR. The path from P2 to P4 can be calculated with a reward of the sum of the Fourier coefficient magnitudes of each point P2 (37) and P4 (23) but now a penalty of −2 can be imposed representing one vertical jump (from heart rate of 114 to heart rate of 112). Finally, the path length from P3 to P4 can be calculated by adding the Fourier coefficient magnitudes of points P3 (40) to P4 (23) but now applying a penalty of −4. The jump penalty has now increased relative to the penalty applied in going from point P2 to P4 since the (vertical) jump from P3 to P4 is now two steps with jump one being from heart rate of 110 to 112, and jump two being from heart rate of 112 to 114. The results are tabulated in FIG. 10A.

Next, at step 182, the largest path length representing the highest score based on the computations of step 180 can be selected. In reference to FIGS. 9A and 10A, these selected highest scores are the circled scores in FIG. 10A, namely, 59, 77 and 78 shown below their respective points P4, P5 and P6 of FIG. 9A.

In step 184, the next data sample can be taken and the index i can be increment by one.

In step 186, the reward/penalty algorithm can be used to determine highest score Fourier coefficient magnitude for each point at time t(i+1) by adding Fourier coefficient magnitude of each end point at time t(i+1) with highest path score of each point at time t(i), and applying a penalty for points requiring heart rate jumps at or above a preset value where the penalty increases with the size of the jump. The penalty can be chosen in some examples to be −2 for a jump of one vertical distance, −4 for two vertical distances, and −9 for three vertical distances. It is noted that there is a difference between the calculation in step 180 and 186. In step 180, since there is not yet determined any highest previous path score, the Fourier coefficient magnitudes of the two points defining the origin and end points can simply be summed. In step 186, there is already a highest path score calculated at time t(i) (corresponding to the circled values in FIGS. 10A, 10B and 10C), and thus these previously determined highest scores at time t(i) can be added to the Fourier coefficient magnitudes at the end points at time t(i+1).

As a specific example and in reference to FIGS. 9B and 10B, the reward/penalty algorithm of step 186 can be applied to points of the time samples ending at time=3 and originating at time t=2.

Taking the end point P7 as a representative example, the path lengths for the three originating points feeding P7 are:

P4-P7 calculated as the sum (reward) of the prior highest score ending in P4 (59) with the Fourier coefficient magnitude at point P7 (26) for a total of 85;

P5-P7 calculated as the sum (reward) of the prior highest score ending in P5 (77) with the Fourier coefficient magnitude at point P (26) minus a penalty of 2 representing one vertical jump for a total of 101; and P6-P7 calculated as the sum (reward) of the prior highest score ending in P6 (78) with the Fourier coefficient magnitude at point P (26) minus a penalty of 4 representing two vertical jumps for a total of 100.

In step 188, it can be determined whether or not the current data sample is the last one or whether additional samples are to be considered. If there are additional samples, the program returns to step 184 where the new sample is obtained and the index i is incremented by one.

If the last sample has been processed in step 188, the program returns to the calling program corresponding to one of step 124 of FIG. 12, step 144 of FIG. 13 and step 164 of FIG. 14.

System Architecture

Figure 16:
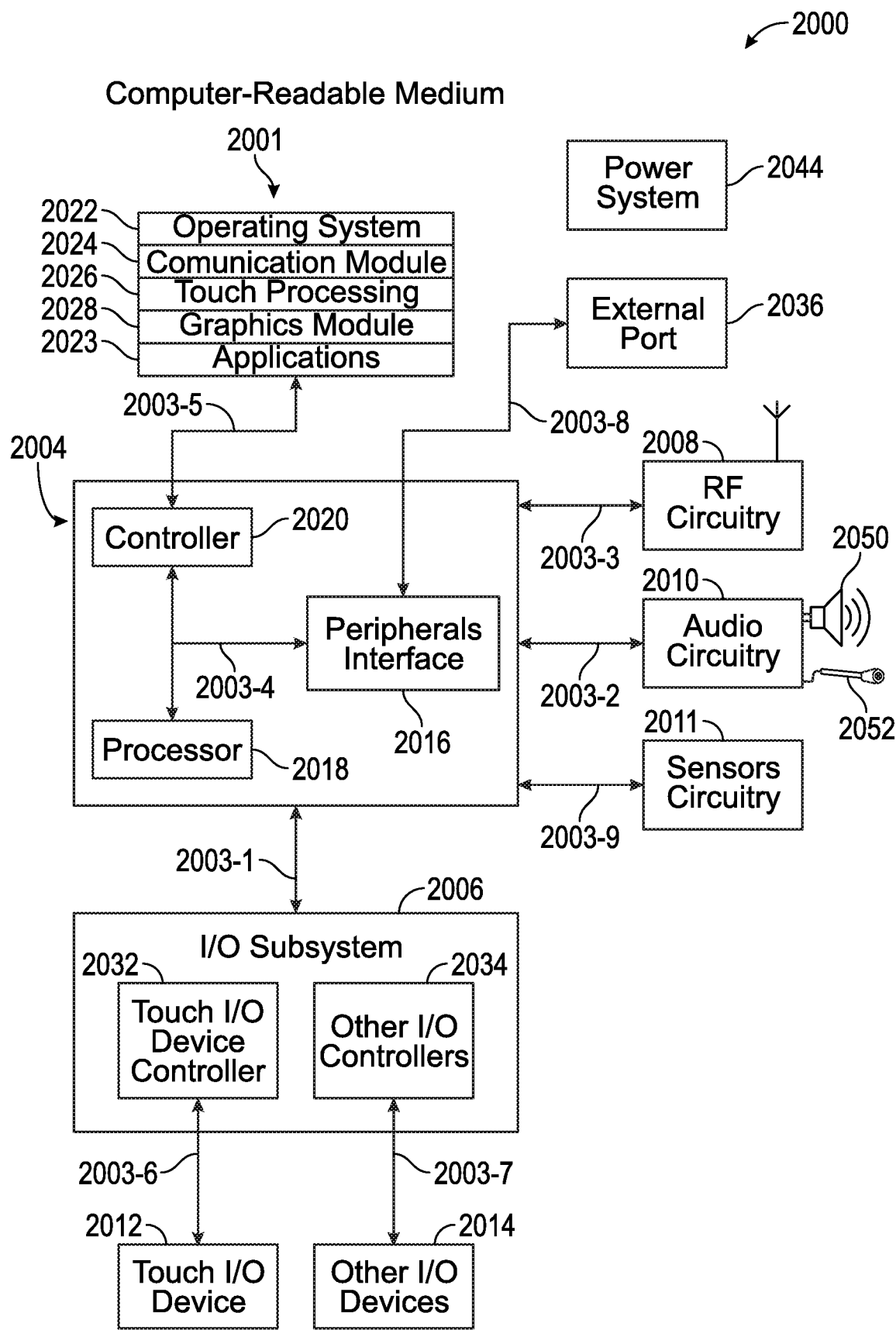
FIG. 16 is a block diagram illustrating an example of a system architecture that may be embodied within any portable or non-portable device according to examples of the disclosure.

Attention is now directed towards examples of a system architecture that may be embodied within any portable or non-portable device including but not limited to a wearable device (smart band, health band, smart watch); a communication device (e.g. mobile phone, smart phone), a multimedia device (e.g., MP3 player, TV, radio), a portable or handheld computer (e.g., tablet, netbook, laptop), a desktop computer, an All-In-One desktop, a peripheral device, or any other system or device adaptable to the inclusion of system architecture 2000, including combinations of two or more of these types of devices. FIG. 16 is a block diagram of one example of system 2000 that generally includes one or more computer-readable mediums 2001, processing system 2004, I/O subsystem 2006, radio frequency (RF) circuitry 2008, audio circuitry 2010, and sensors circuitry 2011. These components may be coupled by one or more communication buses or signal lines 2003.

It should be apparent that the architecture shown in FIG. 16 is only one example architecture of system architecture 2000, and that system architecture 2000 could have more or fewer components than shown, or a different configuration of components. The various components shown in FIG. 16 can be implemented in hardware, software, firmware or any combination thereof, including one or more signal processing and/or application specific integrated circuits.

RF circuitry 2008 can be used to send and receive information over a wireless link or network to one or more other devices and includes well-known circuitry for performing this function. RF circuitry 2008 and audio circuitry 2010 can be coupled to processing system 2004 via peripherals interface 2016. Interface 2016 can include various known components for establishing and maintaining communication between peripherals and processing system 2004. Audio circuitry 2010 can be coupled to audio speaker 2050 and microphone 2052 and can include known circuitry for processing voice signals received from interface 2016 to enable a user to communicate in real-time with other users. In some examples, audio circuitry 2010 can include a headphone jack (not shown). Sensors circuitry 2011 can be coupled to various sensors including, but not limited to, one or more Light Emitting Diodes (LEDs) or other light emitters, one or more photodiodes or other light sensors, one or more photothermal sensors, a magnetometer, an accelerometer, a gyroscope, a barometer, a compass, a proximity sensor, a camera, an ambient light sensor, a thermometer, a GPS sensor, and various system sensors which can sense remaining battery life, power consumption, processor speed, CPU load, and the like.

Peripherals interface 2016 can couple the input and output peripherals of the system 2000 to one or more processor 2018 and one or more computer-readable mediums 2001 via a controller 2020. The one or more processors 2018 communicate with the one or more computer-readable mediums 2001 via the controller 2020. The one more computer-readable mediums 2001 can be any device or medium that can store code and/or data for use by the one or more processors 2018. In some examples, medium 2001 can be a non-transitory computer-readable storage medium. Medium 2001 can include a memory hierarchy, including but not limited to cache, main memory and secondary memory. The memory hierarchy can, as non-limiting examples, be implemented using any combination of RAM (e.g., SRAM, DRAM, DDRAM), ROM, FLASH, magnetic and/or optical storage devices, such as disk drives, magnetic tape, CDs (compact disks) and DVDs (digital video discs). Medium 2001 may also include a transmission medium for carrying information-bearing signals indicative of computer instructions or data (with or without a carrier wave upon which the signals are modulated). For example, the transmission medium may include a communications network, including but not limited to the Internet (also referred to as the World Wide Web), intranet(s), Local Area Networks (LANs), Wide Local Area Networks (WLANs), Storage Area Networks (SANs), Metropolitan Area Networks (MAN) and the like.

One or more processors 2018 can run various software components stored in medium 2001 to perform various functions for system architecture 2000. In some examples, the software components can include operating system 2022, communication module (or set of instructions) 2024, touch processing module (or set of instructions) 2026, graphics module (or set of instructions) 2028, and one or more applications (or set of instructions) 2023. Each of these modules and above noted applications can correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules may be combined or otherwise rearranged in various examples. In some examples, medium 2001 may store a subset of the modules and data structures identified above. Furthermore, medium 2001 may store additional modules and data structures not described above.

Operating system 2022 can include various procedures, sets of instructions, software components and/or drivers for controlling and managing general system tasks (e.g., memory management, storage device control, power management, etc.) and facilitates communication between various hardware and software components.

Communication module 2024 can facilitate communication with other devices over one or more external ports 2036 or via RF circuitry 2008 and can include various software components for handling data received from RF circuitry 2008 and/or external port 2036.

Graphics module 2028 can include various known software components for rendering, animating and displaying graphical objects on a display surface. In examples in which touch I/O device 2012 is a touch sensing display (e.g., touch screen), graphics module 2028 can include components for rendering, displaying, and animating objects on the touch sensing display. The touch I/O device 2012 and/or the other I/O device 2014 may comprise the I/O unit 10 of FIG. 1 or the output unit 42 of FIG. 2, and may also incorporate a UI interface permitting a use to select among programming modes of displaying heart rate data when the I/O device is incorporated into a device 12 of FIG. 1. Further, in relation to FIG. 1, the light emitter 2 and light sensor 4 may be part of the I/O device 2014, and the touch screen 20 may correspond to the touch I/O device 2012 of FIG. 16. The I/O unit 10 either integral within device 12 or via coupling to microphone/speaker 22 may also provide audio outputs as part of the user communications corresponding to audio circuitry 2010 of FIG. 16. Microphone 2052 of FIG. 16 corresponds to the microphone/speaker unit 22 of FIG. 1.

One or more applications 2023 can include any applications installed on system 2000, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player, etc.

Touch processing module 2026 can include various software components for performing various tasks associated with touch I/O device 2012 including but not limited to receiving and processing touch input received from touch I/O device 2012 via touch I/O device controller 2032.

I/O subsystem 2006 can be coupled to touch I/O device 2012 and one or more other I/O devices 2014 for controlling or performing various functions. Touch I/O device 2012 can communicate with processing system 2004 via touch I/O device controller 2032, which can include various components for processing user touch input (e.g., scanning hardware). One or more other input controllers 2034 can receive/send electrical signals from/to other I/O devices 2014. Other I/O devices 2014 may include physical buttons, dials, slider switches, sticks, keyboards, touch pads, additional display screens, or any combination thereof.

If embodied as a touch screen, touch I/O device 2012 can display visual output to the user in a GUI. The visual output may include text, graphics, video, and any combination thereof. Some or all of the visual output may correspond to user-interface objects. Touch I/O device 2012 can form a touch sensing surface that accepts touch input from the user. Touch I/O device 2012 and touch screen controller 2032 (along with any associated modules and/or sets of instructions in medium 2001) can detect and track touches or near touches (and any movement or release of the touch) on touch I/O device 2012 and can convert the detected touch input into interaction with graphical objects, such as one or more user-interface objects. In the case in which device 2012 is embodied as a touch screen, the user can directly interact with graphical objects that are displayed on the touch screen. Alternatively, in the case in which device 2012 is embodied as a touch device other than a touch screen (e.g., a touch pad), the user may indirectly interact with graphical objects that are displayed on a separate display screen embodied as I/O device 2014.

Touch I/O device 2012 may be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1.

In examples for which touch I/O device 2012 is a touch screen, the touch screen may use LCD (liquid crystal display) technology, LPD (light emitting polymer display) technology, OLED (organic LED), or OEL (organic electro luminescence), although other display technologies may be used in other examples.

Feedback may be provided by touch I/O device 2012 based on the user's touch input as well as a state or states of what is being displayed and/or of the computing system. Feedback may be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

System architecture 2000 can also include power system 2044 for powering the various hardware components and may include a power management system, one or more power sources, a recharging system, a power failure detection circuit, a power converter or inverter, a power status indicator and any other components typically associated with the generation, management and distribution of power in portable devices.

In some examples, peripherals interface 2016, one or more processors 2018, and memory controller 2020 of the processing system 2004 can be implemented on a single chip. In some other examples, they may be implemented on separate chips.

Examples of the disclosure can be advantageous in allowing for an electronic device to obtain a respiratory rate signal from a PPG signal, making for a more accurate reading of respiratory rate without directly monitoring breathing.

Examples of the disclosure may be characterized as a device for determining a heart rate (HR) of a user. The device may include a (HR) sensor configured for providing HR signals; an accelerometer coupled to the user's body; and processing circuitry capable of providing HR values that have been compensated for artifacts from acceleration on the HR signals as measured by the accelerometer; the HR values provided for each of a plurality of times over a time interval, and selecting a path of optimum HR values across the time interval, the selected path implementing a reward for candidate paths based on a sum of probabilities of a most probable path between consecutive points of candidate paths, and implementing a penalty based on differences between HR values of the consecutive points along the candidate paths.

The processing circuitry of the device may further transform the HR signals into frequency domain HR signals (FDHR signals) and add together at least a fundamental and first harmonic of Fourier component magnitudes of the FDHR signals corresponding to the HR signals to provide a harmonic boost. The Fourier component magnitudes are absolute values of Fourier coefficients of the FDHR signals. A filter may be used to provide low pass filtering of the Fourier component magnitudes of the FDHR signals and the low pass filtering may be performed using utilizing a Gaussian convolution. Further, the processing circuitry may be capable of providing a peak boost to Fourier component magnitudes of the FDHR signals, and the peak boost may be such as to multiply each local maxima of the Fourier component magnitudes by a number larger than one.

The Fourier component magnitudes are absolute values of Fourier coefficients of the FDHR signals.

The processing circuitry provides the HR values and is capable of transforming the HR signals into frequency domain HR signals (FDHR signals), and transforming signals from the accelerometer into the frequency domain to provide frequency domain artifact signals (FDART signals). The HR values are computed based on complex conjugates of Fourier transform coefficients of the FDHR signals and the complex conjugates of Fourier transform coefficients of the FDART signals. An analog to digital converter may be configured for converting the HR signals and signals from the accelerometer to digital signals or the conversion may be performed within the processing circuitry.

The processing circuitry identifies peak values in the Fourier coefficient magnitudes of the FDART signals and replaces the identified peak values by interpolated values based on values on opposite sides of the identified peak values and utilizing the interpolated values for compensating for artifacts from acceleration.

Examples of the disclosure may be characterized as a device for determining a heart rate (HR) of a use. The device includes a HR sensor configured for providing time domain HR signals, the time domain HR signals having time domain HR components indicative of a user's HR and time domain artifact components indicative of user acceleration movements. The device also includes an accelerometer providing time domain accelerometer output signals and processing circuitry. The processing circuitry is capable of converting the time domain HR signals into frequency domain HR (FDHR) signal magnitudes and converting the time domain accelerometer output signal into frequency domain accelerometer (FDA) signal magnitudes, the FDHR signal magnitudes having frequency domain HR (FDHR) component magnitudes corresponding to a user's heart rate and frequency domain artifact (FDART) component magnitudes corresponding to the FDA signals. The processing circuitry is further capable of compensating for the FDART component magnitudes in the FDHR signal magnitudes to provide compensated FDHR component magnitudes for each of a plurality of times over a time interval; and selecting a path of optimum HR values across the time interval based on the compensated FDHR component magnitudes for each of the plurality of times, the path selecting implementing a reward for candidate paths based on a sum of the compensated FDHR component magnitudes of all points the candidate paths pass through, and a penalty based on a sum of distances between consecutive compensated FDHR component magnitudes along the candidate paths, the distances measured by differences between the HR values associated with consecutive path points.

The processing circuitry is further capable of providing a harmonic boost to the compensated FDHR component magnitudes by adding together at least the fundamental and first harmonic of the compensated FDHR component magnitudes. The processing circuitry is further capable of providing low pass filtering of the compensated FDHR component magnitudes. The low pass filtering can be provided by utilizing a Gaussian convolution. The processing circuitry is further capable of providing a peak boost to each peak of the compensated FDHR component magnitudes. The peak boost can, for example, multiply each local maxima of the compensated FDHR component magnitudes by a number larger than 1.

The device can digitize the time domain HR signals and the time domain accelerometer output signals using an analog to digital converter and can subsequently, utilizing Fourier transformations, convert the digitized time domain HR signals into FDHR signal magnitudes and convert the digitized time domain accelerometer output signal into FDA signal magnitudes.

The processing circuitry of the device is capable of compensating for the FDART component magnitudes to provide the FDHR component magnitudes for each of a plurality of times over the time interval by identifying peak values in the FDART component magnitudes that exceed a first threshold and replacing the identified peak values by interpolated values based on values on opposite sides of the identified peak values and utilizing the interpolated values for compensating for artifacts from acceleration.

Examples of the disclosure may be seen to encompass a method of determining a HR of a user by providing heart rate (HR) signals from a HR sensor configured to be positioned on or closely adjacent a user's skin; providing accelerometer output signals from an accelerometer coupled to the user body; providing HR values based on compensating for artifacts in the HR signals, the artifacts determined from the accelerometer output signals, the HR values provided for each of a plurality of times over a time interval; and selecting a path of optimum HR values across the time interval, the selected path implementing a reward for candidate paths based on a sum of the probabilities of the most probable path between consecutive points of candidate paths, and a penalty based on differences between HR values of the consecutive points along the candidate paths.

The disclosure may also be seen to encompass a non-transitory computer readable medium, the computer readable medium containing instructions that, when executed, perform a method for operating an electronic device, the electronic device including a processor, the non-transitory computer readable medium, at least one light emitter, at least one light receive and an accelerometer. The method can comprise emitting light from the at least one light emitter; receiving light by the at least one light receiver; receiving heart rate (HR) signals based on light received by the at least one light receiver; receiving accelerometer output signals from the accelerometer; providing HR values based on compensating for artifacts in the HR signals, the artifacts determined from the accelerometer output signals the HR values provided for each of a plurality of time values over a time interval; and selecting a path of optimum HR values across the time interval, the selected path implementing a reward for candidate paths based on a sum of the probabilities of the most probable path between consecutive points of candidate paths, and a penalty based on differences between HR values of the consecutive points along the candidate paths.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. A device for determining a heart rate (HR) of a user comprising:
 a HR sensor configured to be worn by a user and comprising a photoplethysmogram (PPG) sensor configured to output PPG signals;
 a display configured to provide a graphical output; and
 a processor configured to:
  sample the PPG signals over a first time period to generate a first set of data points;
  determine, from the first set of data points, a first set of HR values corresponding to a first time;
  select a first path of HR values in accordance with a criteria, wherein selecting the first path includes selecting a first HR value of the first set of HR values;
  cause the display to display at least one of the selected first path of HR values;
  sample the PPG signals over a second time period to generate a second set of data points;
  determine, from the second set of data points, a second set of HR values corresponding to the second time;
  select a second path of HR values in accordance with the criteria, wherein selecting the second path includes:
   selecting a second HR value from the first set of HR values that is different than the first HR value in the first path of HR values; and
   selecting a third HR value from the second set of HR values; and
  cause the display to display at least the second HR value of the selected second path of HR values.

2. The device of claim 1, wherein the criteria is based on consecutive Fourier coefficient magnitudes of corresponding consecutive HR values along each of the first path of HR values and the second path of HR values and differences in corresponding consecutive HR values along each of the first path of HR values and the second path of HR values.

3. The device of claim 2, wherein the processor determines the first set of HR values by transforming the first set of data points into frequency domain HR signals (FDHR signals) and determining and adding together at least a fundamental and first harmonic of Fourier component magnitudes of the FDHR signals corresponding to the first set of data points.

4. The device of claim 3, wherein the Fourier component magnitudes are absolute values of Fourier coefficients of the FDHR signals.

5. The device of claim 1, wherein determining the first set of HR values includes transforming the first set of data points into frequency domain HR signals (FDHR signals) and low pass filtering Fourier component magnitudes of the FDHR signals.

6. The device of claim 5, wherein the low pass filtering is provided by utilizing a Gaussian convolution.

7. The device of claim 1, wherein determining the first set of HR values includes transforming the first set of data points into frequency domain HR signals (FDHR signals) and providing a peak boost to Fourier component magnitudes of the FDHR signals.

8. The device of claim 7, wherein the peak boost multiplies each local maxima of the Fourier component magnitudes by a number larger than 1.

9. The device of claim 8, wherein the Fourier component magnitudes are absolute values of Fourier coefficients of the FDHR signals.

10. The device of claim 1, wherein determining the first set of HR values includes transforming the first set of data points into frequency domain HR signals (FDHR signals) and adding together at least a fundamental and first harmonic of Fourier component magnitudes of the FDHR signals corresponding to the HR signals to provide a harmonic boost and further providing a peak boost to Fourier component magnitudes of the FDHR signals by multiplying local maxima of the Fourier component magnitudes by a number larger than 1.

11. A method for determining a user's heart rate (HR) using a physiological sensing device, comprising:
 detecting PPG signals using a photoplethysmogram (PPG) sensor of the physiological sensing device;
 at a processor of the physiological sensing device:
  sampling the PPG signals over a first time period to generate a first set of data points;
  determining, from the first set of data points, a first set of HR values corresponding to a first time;
  selecting a first path of HR values in accordance with a given criteria, wherein selecting the first path includes selecting a first HR value of the first set of HR values;
  sampling the PPG signals over a second time period to generate a second set of data points;
  determining, from the second set of data points, a second set of HR values corresponding to a second time;
  selecting a second path of HR values in accordance with the given criteria, wherein selecting the second path includes:
   selecting a second HR value from the first set of HR values that is different that the first HR value in the first path of HR values; and
   selecting a third HR value from the second set of HR values.

12. The method of claim 11, wherein the given criteria is based on consecutive Fourier coefficient magnitudes of corresponding consecutive HR values along each of the first path of HR values and the second path of HR values and differences in consecutive HR values along each of the first path of HR values and the second path of HR values.

13. The method of claim 12, wherein determining the first set of HR values comprises transforming the first set of data points into frequency domain HR signals (FDHR signals) and determining and adding together at least a fundamental and first harmonic of Fourier component magnitudes of the FDHR signals corresponding to the first set of data points.

14. The method of claim 13, wherein the Fourier component magnitudes are absolute values of Fourier coefficients of the FDHR signals.

15. The method of claim 11, wherein determining the first set of HR values comprises transforming the first set of data points into frequency domain HR signals (FDHR signals) and low pass filtering Fourier component magnitudes of the FDHR signals.

16. The method of claim 15, wherein the low pass filtering is provided by utilizing a Gaussian convolution.

17. The method of claim 11, wherein determining the first set of HR values comprises transforming the HR signals into frequency domain HR signals (FDHR signals) and providing a peak boost to Fourier component magnitudes of the FDHR signals.

18. The method of claim 17, wherein the peak boost multiplies each local maxima of the Fourier component magnitudes by a number larger than 1.

19. The method of claim 18, wherein the Fourier component magnitudes are absolute values of Fourier coefficients of the FDHR signals.

20. The method of claim 11, wherein determining the first set of HR values comprises transforming the first set of data points into frequency domain HR signals (FDHR signals) and adding together at least a fundamental and first harmonic of Fourier component magnitudes of the FDHR signals corresponding to the HR signals to provide a harmonic boost and further providing a peak boost to Fourier component magnitudes of the FDHR signals by multiplying local maxima of the Fourier component magnitudes by a number larger than 1.

\* \* \* \* \*